US005650306A

United States Patent [19]
Nabel et al.

[11] Patent Number: 5,650,306
[45] Date of Patent: Jul. 22, 1997

[54] RECOMBINANT NUCLEIC ACIDS FOR INHIBITING HIV GENE EXPRESSION

[75] Inventors: Gary J. Nabel; Zhi-Yong Yang, both of Ann Arbor, Mich.; Jinsong Liu, Randolph, N.J.; Clive Woffendin, Ann Arbor, Mich.

[73] Assignee: University of Michigan, Ann Arbor, Mich.

[21] Appl. No.: 73,836

[22] Filed: Jun. 7, 1993

[51] Int. Cl.$^6$ .......................... C12N 15/11; C12N 15/63; C12N 15/86; C07H 21/04
[52] U.S. Cl. .................. 435/172.3; 435/320.1; 536/23.72; 536/24.1; 536/24.5
[58] Field of Search .................. 435/69.1, 69.2, 435/172.1, 240.2, 320.1, 172.3; 536/23.1, 23.4, 23.72, 24.1

[56] References Cited

FOREIGN PATENT DOCUMENTS 406557   1/1991   European Pat. Off. ........ C12N 15/49

OTHER PUBLICATIONS

Woffendin et al., "Nonviral and Viral Delivery of a Human Immunodeficiency Virus Protective Gene Into Primary Human T Cells", PNAS, vol. 91, Nov. 1994, pp. 11581–11585.

Malim, Michael H. and Cullen, Bryan R. "HIV–1 Structural Gene Expression Requires the Binding of Multiple Rev Monomers to the Viral RRE: Implications for HIV–1 Latency." Cell 65:241–248 (1991).

Malim, Michael H. et al. "Stable Expression of Transdominant Rev Protein in Human T Cells Inhibits Human Immunodeficiency Virus Replication." J. Exp. Med. 176:1197–1201 (1992).

Sullenger, Bruce A. et al. "Overexpression of TAR Sequences Renders Cells Resistant to Human Immunodeficiency Virus Replication." Cell 63:601–608 (1990).

Lin, Wen–chang and Culp, Lloyd, A. "Selectable Plasmid Vectors with Alternative and Ultrasensitive Histochemical Marker Genes." BioTechniques 11:344–351 (1991).

Malim, Michael H. et al. "Functional Dissection of the HIV–1 Rev Trans–Activator–Derivation of a Trans–Dominant Repressor of Rev Function." Cell 58:205–214 (1989).

*Primary Examiner*—David Guzo
*Attorney, Agent, or Firm*—Campbell & Flores LLP

[57] ABSTRACT

This invention provides recombinant nucleic acid molecules for enhanced expression of genes that inhibit HIV gene expression. Cells transfected with these recombinant nucleic acids exhibit prolonged cell life. This invention also provides methods of treating individuals infected with HIV by introducing into them the transfected cells of this invention.

10 Claims, 19 Drawing Sheets pLJ Rev m10 retroviral vector

| Region | | From | To | Description |
|---|---|---|---|---|
| 5' LTR | (U3) | 1 | 448 | U3 region of MoMuLV |
| | (R) | 449 | 516 | R region of MoMuLV |
| | (U5) | 517 | 594 | U5 region of MoMuLV |
| trans. init. | | 449 | | mRNA |
| psi region | | 449 | 1031 | untranslated/packaging |
| rev M10 | | 1037 | 1636 | Rev M10 orf |
| SVneo | | 1637 | 3302 | pSV2neo |
| pBR322 | | 3303 | 3885 | ori |
| 3'LTR/flank | | 3886 | 5109 | 3' flank + LTR |

Pljrevml.Seq  Length: 5109  April 8, 1993  19:47  Type: N  Check: 215 ..

```
  1 AATGAAAGAC CCCACCTGTA GGTTTGGCAA GCTAGCTTAA GTAACGCCAT
 51 TTTGCAAGGC ATGGAAAAAT ACATAACTGA GAATAGAGAA GTTCAGATCA
101 AGGTCAGGAA CAGATGGAAC AGCTGAATAT GGGCCAAACA GGATATCTGT
151 GGTAAGCAGT TCCTGCCCCG GCTCAGGGCC AAGAACAGAT GGAACAGCTG
201 AATATGGGCC AAACAGGATA TCTGTGGTAA GCAGTTCCTG CCCCGGCTCA
251 GGGCCAAGAA CAGATGGTCC CCAGATGCGG TCCAGCCCTC AGCAGTTTCT
301 AGAGAACCAT CAGATGTTTC CAGGGTGCCC CAAGGACCTG AAATGACCCT
351 GTGCCTTATT TGAACTAACC AATCAGTTCG CTTCTCGCTT CTGTTCGCGC
401 GCTTCTGCTC CCCGAGCTCA ATAAAAGAGC CCACAACCCC TCACTCGGGG
451 CGCCAGTCCT CCGATTGACT GAGTCGCCCG GGTACCCGTG TATCCAATAA
501 ACCCTCTTGC AGTTGCATCC GACTTGTGGT CTCGCTGTTC CTTGGGAGGG
551 TCTCCTCTGA GTGATTGACT ACCCGTCAGC GGGGGTCTTT CATTTGGGGG
601 CTCGTCCGGG ATCGGGAGAC CCCTGCCCAG GGACCACCGA CCCACCACCG
651 GGAGGTAAGC TGGCCAGCAA CTTATCTGTG TCTGTCCGAT TGTCTAGTGT
701 CTATGACTGA TTTTATGCGC CTGCGTCGGT ACTAGTTAGC TAACTAGCTC
751 TGTATCTGGC GGACCCGTGG TGGAACTGAC GAGTTCGGAA CACCCGGCCG
```

FIG. 4A

```
 801  CAACCCTGGG AGACGTCCCA GGGACTTCGG GGGCCGTTTT TGTGGCCCGA
 851  CCTGAGTCCA AAAATCCCGA TCGTTTTGGA CTCTTTGGTG CACCCCCCTT
 901  AGAGGAGGGA TATGTGGTTC TGGTAGGAGA CGAGAACCTA AAACAGTTCC
 951  CGCCTCCGTC TGAATTTTTG CTTTCGGTTT GGGACCGAAG CCGCGCCGCG
1001  CGTCTTGTCT GCTGCAGCAT CGTTCTGTGT TGGATCCCAT GGCAGGAAGA
1051  AGCGGAGACA GCGACGAAGA CCTCCTCAAG GCAGTCAGAC TCATCAAGTT
1101  TCTCTATCAA AGCAACCCAC CTCCCAATCC CGAGGGGACC CGACAGGCCC
1151  GAAGGAATAG AAGAAGAAGG TGGAGAGAGA GACAGAGACA GATCCATTCG
1201  ATTAGTGAAC GGATCCTTAG CACTTATCTG GGACGATCTG CGAGCCTGTG
1251  CCTCTTCAGC TACCACCAGA TCTGAGACTT ACTCTTGATT GTAACGAGGA
1301  TTGTGGAACT TCTGGGACGC AGGGGGTGGG AAGCCCTCAA ATATTGGTGG
1351  AATCTCCTAC AGTATTGGAG TCAGGAACTA AGAATAGTG  CTGTTAGCTT
1401  GCTCAATGCC ACAGCTATAG CAGTAGCTGA GGGGACAGAT AGGGTTATAG
1451  AAGTAGTACA AGAAGCTTGT AGAGCTATTC GCCACATACC TAGAAGAATA
1501  AGACAGGGCT TGGAAAGGAT TTTGCTATAA GATGGGTGGC AAGTGGTCAA
1551  AAAGTAGTGT GATTGGATGG CTTACTGTAA GGGAAAGAAT GAGACGAGCT
1601  GAGCCAGCAG CAGATGGGGT GGGAGCAGCA TCTCGAGCAG CTGTGGAATG
1651  TGTGTCAGTT AGGGTGTGGA AAGTCCCCAG GCTCCCCAGC AGGCAGAAGT
1701  ATGCAAAGCA TGCATCTCAA TTAGTCAGCA ACCAGGTGTG GAAAGTCCCC
1751  AGGCTCCCCA GCAGGCAGAA CTATGCAAAG CATGCATCTC AATTAGTCAG
1801  CAACCATAGT CCCGCCCCTA ACTCCGCCCA TCCCGCCCCT AACTCCGCCC
1851  AGTTCCGCCC ATTCTCCGCC CCATGGCTGA CTAATTTTTT TTATTTATGC
1901  AGAGGCCGAG GCCGCCTCGG CCTCTGAGCT ATTCCAGAAG TATTGAGGAG
1951  GCTTTTTTGG AGGCCTAGGC TTTTGCAAAA AGCTTCACGC TGCCGCAAGC
2001  ACTCAGGGCG CAAGGGCTGC TAAAGGAAGC GGAACACGTA GAAAGCCAGT
2051  CCGCAGAAAC GGTGCTGACC CCGGATGAAT GTCAGCTACT GGGCTATCTG
2101  GACAAGGGAA AACGCAAGCG CAAAGAGAAA GCAGGTAGCT TGCAGTGGGC
```

FIG. 4B

```
2151  TTACATGGCG ATAGCTAGAC TGGGCGGTTT TATGGACAGC AAGCGAACCG
2201  GAATTGCCAG CTGGGGCGCC CTCTGGTAGC CCTGCAAAGC CCTGCAAAGT
2251  AAACTGGATG GCTTTCTTGC CGCCAAGGAT CTGATGGCGC AGGGGATCAA
2301  GATCTGATCA AGAGACAGGA TGAGGATCGT TTCGCATGAT TGAACAAGAT
2351  GGATTGCACG CAGGTTCTCC GGCCGCTTGG GTGGAGAGGC TATTCGGCTA
2401  TGACTGGGCA CAACAGACAA TCGGCTGCTC TGATGCCGCC GTGTTCCGGC
2451  TGTCAGCGCA GGGGCGCCCG GTTCTTTTTG TCAAGACCGA CCTGTCCGGT
2501  GCCCTGAATG AACTGCAGGA CGAGGCAGCG CGGCTATCGT GGCTGGCCAC
2551  GACGGGCGTT CCTTGCGCAG CTGTGCTCGA CGTTGTCACT GAAGCGGGAA
2601  GGGACTGGCT GCTATTGGGC GAAGTGCCGG GGCAGGATCT CCTGTCATCT
2651  CACCTTGCTC CTGCCGAGAA AGTATCCATC ATGGCTGATG CAATGCGGCG
2701  GCTGCATACG CTTGATCCGG CTACCTGCCC ATTCGACCAC CAAGCGAAAC
2751  ATCGCATCGA GCGAGCYCGT ACTCGGATGG AAGCCGGTCT TGTCGATCAG
2801  GATGATCTGG ACGAAGAGCA TCAGGGGCTC GCGCCAGCCG AACTGTTCGC
2851  CAGGCTCAAG GCGCGCATGC CCGACGGCGA GGATCTCGTC GTGACCCATG
2901  GCGATGCCTG CTTGCCGAAT ATCATGGTGG AAAATGGCCG CTTTTCTGGA
2951  TTCATCGACT GTGGCCGGCT GGGTGTGGCG GACCGCTATC AGGACATAGC
3001  GTTGGCTACC CGTGATATTG CTGAAGAGCT TGGCGGCGAA TGGGCTGACC
3051  GCTTCCTCGT GCTTTACGGT ATCGCCGCTC CCGATTCGCA GCGCATCGCC
3101  TTCTATCGCC TTCTTGAGGA GTTCTTCTGA GCGGGACTCT GGGGTTCGAA
3151  ATGACCGACC AAGCGACGCC CAACCTGCCA TCACGAGATT TCGATTCCAC
3201  CGCCGCCTTC TATGAAAGGT TGGGCTTCGG AATCGTTTTC CGGGACGCCG
3251  GCTGGATGAT CCTCCAGCGC GGGGATCTCA TGCTGGAGTT CTTCGCCCAC
3301  CCCCGCGTTG CTGGCGTTTT TCCATAGGCT CCGCCCCCCT GACGAGCATC
3351  ACAAAAATCG ACGCTCAAGT CAGAGGTGGC GAAACCCGAC AGGACTATAA
3401  AGATACCAGG CGTTTCCCCC TGGAAGCTCC CTCGTGCGCT CTCCTGTTCC
3451  GACCCTGCCG CTTACCGGAT ACCTGTCCGC CTTTCTCCCT TCGGGAAGCG
```

FIG. 4C

```
3501  TGGCGCTTTC TCATAGCTCA CGCTGTAGGT ATCTCAGTTC GGTGTAGGTC
3551  GTTCGCTCCA AGCTGGGCTG TGTGCACGAA CCCCCCGTTC AGCCCGACCG
3601  CTGCGCCTTA TCCGGTAACT ATCGTCTTGA GTCCAACCCG GTAAGACACG
3651  ACTTATCGCC ACTGGCAGCA GCCACTGGTA ACAGGATTAG CAGAGCGAGG
3701  TATGTAGGCG GTGCTACAGA GTTCTTGAAG TGGTGGCCTA ACTACGGCTA
3751  CACTAGAAGG ACAGTATTTG GTATCTGCGC TCTGCTGAAG CCAGTTACCT
3801  TCGGAAAAAG AGTTGGTAGC TCTTGATCCG GCAAACAAAC CACCGCTGGT
3851  AGCGGTGGTT TTTTTGTTTG CAAGCAGCAG ATTACGTCGG TGTCGTTAAC
3901  CCTGGCCCTA TTATTGGGTG GACTAACCAT GGGGGGAATT GCCGCTGGAA
3951  TAGGAACAGG GACTACTGCT CTAATGGCCA CTCAGCAATT CCAGCAGCTC
4001  CAAGCCGCAG TACAGGATGA TCTCAGGGAG GTTGAAAAAT CAATCTCTAA
4051  CCTAGAAAAG TCTCTCACTT CCCTGTCTGA AGTTGTCCTA CAGAATCGAA
4101  GGGGCCTAGA CTTGTTATTT CTAAAAGAAG GAGGGCTGTG TGCTGCTCTA
4151  AAAGAAGAAT GTTGCTTCTA TGCGGACCAC ACAGGACTAG TGAGAGACAG
4201  CATGGCCAAA TTGAGAGAGA GGCTTAATCA GAGACAGAAA CTGTTTGAGT
4251  CAACTCAAGG ATGGTTTGAG GGACTGTTTA ACAGATCCCC TTGGTTTACC
4301  ACCTTGATAT CTACCATTAT GGGACCCCTC ATTGTACTCC TAATGATTTT
4351  GCTCTTCGGA CCCTGCATTC TTAATCGATT AGTCCAATTT GTTAAAGACA
4401  GGATATCAGT GGTCCAGGCT CTAGTTTTGA CTCAACAATA TCACCAGCTG
4451  AAGCCTATAG AGTACGAGCC ATAGATAAAA TAAAAGATTT TATTTAGTCT
4501  CCAGAAAAAG GGGGGAATGA AGACCCCAC CTGTAGGTTT GGCAAGCTAG
4551  CTTAAGTAAC GCCATTTTGC AAGGCATGGA AAAATACATA ACTGAGAATA
4601  GAGAAGTTCA GATCAAGGTC AGGAACAGAT GGAACAGCTG AATATGGGCC
4651  AAACAGGATA TCTGTGGTAA GCAGTTCCTG CCCCGGCTCA GGGCCAAGAA
4701  CAGATGGAAC AGCTGAATAT GGGCCAAACA GGATATCTGT GGTAAGCAGT
4751  TCCTGCCCCG GCTCAGGGCC AAGAACAGAT GGTCCCCAGA TGCGGTCCAG
4801  CCCTCAGCAG TTTCTAGAGA ACCATCAGAT GTTTCCAGGG TGCCCCAAGG
```

FIG. 4D

```
4851  ACCTGAAATG ACCCTGTGCC TTATTTGAAC TAACCAATCA GTTCGCTTCT
4901  CGCTTCTGTT CGCGCGCTTC TGCTCCCCGA GCTCAATAAA AGAGCCCACA
4951  ACCCCTCACT CGGGGCGCCA GTCCTCCGAT TGACTGAGTC GCCCGGGTAC
5001  CCGTGTATCC AATAAACCCT CTTGCAGTTG CATCCGACTT GTGGTCTCGC
5051  TGTTCCTTGG GAGGGTCTCC TCTGAGTGAT TGACTACCCG TCAGCGGGGG
5101  TCTTTCATT
```

FIG. 4E pLJ mutant Rev m10 retroviral vector

| Region | From | To | Description |
|---|---|---|---|
| 5' LTR (U3) | 1 | 448 | U3 region of MoMuLV |
| (R) | 449 | 516 | R region of MoMuLV |
| (U5) | 517 | 594 | U5 region of MoMuLV |
| trans. init. | 449 | | mRNA |
| psi region | 449 | 1031 | untranslated/packaging |
| untranslated | 1037 | 1107 | pre-pro-insulin |
| rev M10 | 1108 | 1703 | Rev M10 orf |
| SVneo | 1704 | 3369 | pSV2neo |
| pBR322 | 3370 | 3952 | ori |
| 3'LTR/flank | 3953 | 5176 | 3' flank + LTR |

Pljdrev.Seq    Length: 5176   April 8, 1993   19:48   Type: N   Check: 185 ..

```
  1 AATGAAAGAC CCCACCTGTA GGTTTGGCAA GCTAGCTTAA GTAACGCCAT
 51 TTTGCAAGGC ATGGAAAAAT ACATAACTGA GAATAGAGAA GTTCAGATCA
101 AGGTCAGGAA CAGATGGAAC AGCTGAATAT GGGCCAAACA GGATATCTGT
151 GGTAAGCAGT TCCTGCCCCG GCTCAGGGCC AAGAACAGAT GGAACAGCTG
201 AATATGGGCC AAACAGGATA TCTGTGGTAA GCAGTTCCTG CCCCGGCTCA
251 GGGCCAAGAA CAGATGGTCC CCAGATGCGG TCCAGCCCTC AGCAGTTTCT
301 AGAGAACCAT CAGATGTTTC CAGGGTGCCC CAAGGACCTG AAATGACCCT
351 GTGCCTTATT TGAACTAACC AATCAGTTCG CTTCTCGCTT CTGTTCGCGC
401 GCTTCTGCTC CCCGAGCTCA ATAAAAGAGC CCACAACCCC TCACTCGGGG
451 CGCCAGTCCT CCGATTGACT GAGTCGCCCG GGTACCCGTG TATCCAATAA
501 ACCCTCTTGC AGTTGCATCC GACTTGTGGT CTCGCTGTTC CTTGGGAGGG
551 TCTCCTCTGA GTGATTGACT ACCCGTCAGC GGGGGTCTTT CATTTGGGGG
601 CTCGTCCGGG ATCGGGAGAC CCCTGCCCAG GGACCACCGA CCCACCACCG
651 GGAGGTAAGC TGGCCAGCAA CTTATCTGTG TCTGTCCGAT TGTCTAGTGT
701 CTATGACTGA TTTTATGCGC CTGCGTCGGT ACTAGTTAGC TAACTAGCTC
```

FIG. 5A

```
 751  TGTATCTGGC GGACCCGTGG TGGAACTGAC GAGTTCGGAA CACCCGGCCG
 801  CAACCCTGGG AGACGTCCCA GGGACTTCGG GGGCCGTTTT TGTGGCCCGA
 851  CCTGAGTCCA AAAATCCCGA TCGTTTTGGA CTCTTTGGTG CACCCCCCTT
 901  AGAGGAGGGA TATGTGGTTC TGGTAGGAGA CGAGAACCTA AAACAGTTCC
 951  CGCCTCCGTC TGAATTTTTG CTTTCGGTTT GGGACCGAAG CCGCGCCGCG
1001  CGTCTTGTCT GCTGCAGCAT CGTTCTGTGT TGGGATCAGC TCGTTTAGTA
1051  AGTCAAGCTT AAGTGACCAG CTACAGTCGG AAACCATCAG CAAGAGGTCA
1101  TTGTTCACGC AGGAAGAAGC GGAGACAGCG ACGAAGACCT CCTCAAGGCA
1151  GTCAGACTCA TCAAGTTTCT CTATCAAAGC AACCCACCTC CCAATCCCGA
1201  GGGGACCCGA CAGGCCCGAA GGAATAGAAG AAGAAGGTGG AGAGAGAGAC
1251  AGAGACAGAT CCATTCGATT AGTGAACGGA TCCTTAGCAC TTATCTGGGA
1301  CGATCTGCGA GCCTGTGCCT CTTCAGCTAC CACCAGATCT GAGACTTACT
1351  CTTGATTGTA ACGAGGATTG TGGAACTTCT GGGACGCAGG GGGTGGGAAG
1401  CCCTCAAATA TTGGTGGAAT CTCCTACAGT ATTGGAGTCA GGAACTAAAG
1451  AATAGTGCTG TTAGCTTGCT CAATGCCACA GCTATAGCAG TAGCTGAGGG
1501  GACAGATAGG GTTATAGAAG TAGTACAAGA AGCTTGTAGA GCTATTCGCC
1551  ACATACCTAG AAGAATAAGA CAGGGCTTGG AAAGGATTTT GCTATAAGAT
1601  GGGTGGCAAG TGGTCAAAAA GTAGTGTGAT TGGATGGCTT ACTGTAAGGG
1651  AAAGAATGAG ACGAGCTGAG CCAGCAGCAG ATGGGGTGGG AGCAGCATCT
1701  CGAGCAGCTG TGGAATGTGT GTCAGTTAGG GTGTGGAAAG TCCCCAGGCT
1751  CCCCAGCAGG CAGAAGTATG CAAAGCATGC ATCTCAATTA GTCAGCAACC
1801  AGGTGTGGAA AGTCCCCAGG CTCCCCAGCA GGCAGAAGTA TGCAAAGCAT
1851  GCATCTCAAT TAGTCAGCAA CCATAGTCCC GCCCCTAACT CCGCCCATCC
1901  CGCCCCTAAC TCCGCCCAGT TCCGCCCATT CTCCGCCCCA TGGCTGACTA
1951  ATTTTTTTTA TTTATGCAGA GGCCGAGGCC GCCTCGGCCT CTGAGCTATT
2001  CCAGAAGTAG TGAGGAGGCT TTTTTGGAGG CCTAGGCTTT TGCAAAAAGC
2051  TTCACGCTGC CGCAAGCACT CAGGGCGCAA GGGCTGCTAA AGGAAGCGGA
```

FIG. 5B

```
2101  ACACGTAGAA AGCCAGTCCG CAGAAACGGT GCTGACCCCG GATGAATGTC
2151  AGCTACTGGG CTATCTGGAC AAGGGAAAAC GCAAGCGCAA AGAGAAAGCA
2201  GGTAGCTTGC AGTGGGCTTA CATGGCGATA GCTAGACTGG GCGGTTTTAT
2251  GGACAGCAAG CGAACCGGAA TTGCCAGCTG GGCGCCCTC TGGTAGCCCT
2301  GCAAAGCCCT GCAAAGTAAA CTGGATGGCT TTCTTGCCGC CAAGGATCTG
2351  ATGGCGCAGG GGATCAAGAT CTGATCAAGA GACAGGATGA GGATCGTTTC
2401  GCATGATTGA ACAAGATGGA TTGCACGCAG GTTCTCCGGC CGCTTGGGTG
2451  GAGAGGCTAT TCGGCTATGA CTGGGCACAA CAGACAATCG GCTGCTCTGA
2501  TGCCGCCGTG TTCCGGCTGT CAGCGCAGGG GCGCCCGGTT CTTTTTGTCA
2551  AGACCGACCT GTCCGGTGCC CTGAATGAAC TGCAGGACGA GGCAGCGCGG
2601  CTATCGTGGC TGGCCACGAC GGGCGTTCCT TGCGCAGCTG TGCTCGACGT
2651  TGTCACTGAA GCGGGAAGGG ACTGGCTGCT ATTGGGCGAA GTGCCGGGGC
2701  AGGATCTCCT GTCATCTCAC CTTGCTCCTG CCGAGAAAGT ATCCATCATG
2751  GCTGATGCAA TGCGGCGGCT GCATACGCTT GATCCGGCTA CCTGCCCATT
2801  CGACCACCAA GCGAAACATC GCATCGAGCG AGCYCGTACT CGGATGGAAG
2851  CCGGTCTTGT CGATCAGGAT GATCTGGACG AAGAGCATCA GGGGCTCGCG
2901  CCAGCCGAAC TGTTCGCCAG GCTCAAGGCG CGCATGCCCG ACGGCGAGGA
2951  TCTCGTCGTG ACCCATGGCG ATGCCTGCTT GCCGAATATC ATGGTGGAAA
3001  ATGGCCGCTT TTCTGGATTC ATCGACTGTG GCCGGCTGGG TGTGGCGGAC
3051  CGCTATCAGG ACATAGCGTT GGCTACCCGT GATATTGCTG AAGAGCTTGG
3101  CGGCGAATGG GCTGACCGCT TCCTCGTGCT TTACGGTATC GCCGCTCCCG
3151  ATTCGCAGCG CATCGCCTTC TATCGCCTTC TTGAGGAGTT CTTCTGAGCG
3201  GGACTCTGGG GTTCGAAATG ACCGACCAAG CGACGCCCAA CCTGCCATCA
3251  CGAGATTTCG ATTCCACCGC CGCCTTCTAT GAAAGGTTGG GCTTCGGAAT
3301  CGTTTTCCGG GACGCCGGCT GGATGATCCT CCAGCGCGGG GATCTCATGC
3351  TGGAGTTCTT CGCCCACCCC CGCGTTGCTG GCGTTTTCC ATAGGCTCCG
3401  CCCCCCTGAC GAGCATCACA AAAATCGACG CTCAAGTCAG AGGTGGCGAA
```

FIG. 5C

```
3451  ACCCGACAGG ACTATAAAGA TACCAGGCGT TTCCCCCTGG AAGCTCCCTC
3501  GTGCGCTCTC CTGTTCCGAC CCTGCCGCTT ACCGGATACC TGTCCGCCTT
3551  TCTCCCTTCG GGAAGCGTGG CGCTTTCTCA TAGCTCACGC TGTAGGTATC
3601  TCAGTTCGGT GTAGGTCGTT CGCTCCAAGC TGGGCTGTGT GCACGAACCC
3651  CCCGTTCAGC CCGACCGCTG CGCCTTATCC GGTAACTATC GTCTTGAGTC
3701  CAACCCGGTA AGACACGACT TATCGCCACT GGCAGCAGCC ACTGGTAACA
3751  GGATTAGCAG AGCGAGGTAT GTAGGCGGTG CTACAGAGTT CTTGAAGTGG
3801  TGGCCTAACT ACGGCTACAC TAGAAGGACA GTATTTGGTA TCTGCGCTCT
3851  GCTGAAGCCA GTTACCTTCG GAAAAAGAGT TGGTAGCTCT TGATCCGGCA
3901  AACAAACCAC CGCTGGTAGC GGTGGTTTTT TTGTTTGCAA GCAGCAGATT
3951  ACGTCGGTGT CGTTAACCCT GGCCCTATTA TTGGGTGGAC TAACCATGGG
4001  GGGAATTGCC GCTGGAATAG GAACAGGGAC TACTGCTCTA ATGGCCACTC
4051  AGCAATTCCA GCAGCTCCAA GCCGCAGTAC AGGATGATCT CAGGGAGGTT
4101  GAAAAATCAA TCTCTAACCT AGAAAAGTCT CTCACTTCCC TGTCTGAAGT
4151  TGTCCTACAG AATCGAAGGG GCCTAGACTT GTTATTTCTA AAAGAAGGAG
4201  GGCTGTGTGC TGCTCTAAAA GAAGAATGTT GCTTCTATGC GGACCACACA
4251  GGACTAGTGA GAGACAGCAT GGCCAAATTG AGAGAGAGGC TTAATCAGAG
4301  ACAGAAACTG TTTGAGTCAA CTCAAGGATG GTTGAGGGA CTGTTTAACA
4351  GATCCCCTTG GTTTACCACC TTGATATCTA CCATTATGGG ACCCCTCATT
4401  GTACTCCTAA TGATTTTGCT CTTCGGACCC TGCATTCTTA ATCGATTAGT
4451  CCAATTTGTT AAAGACAGGA TATCAGTGGT CCAGGCTCTA GTTTTGACTC
4501  AACAATATCA CCAGCTGAAG CCTATAGAGT ACGAGCCATA GATAAAATAA
4551  AAGATTTTAT TTAGTCTCCA GAAAAAGGGG GGAATGAAAG ACCCCACCTG
4601  TAGGTTTGGC AAGCTAGCTT AAGTAACGCC ATTTTGCAAG GCATGGAAAA
4651  ATACATAACT GAGAATAGAG AAGTTCAGAT CAAGGTCAGG AACAGATGGA
4701  ACAGCTGAAT ATGGGCCAAA CAGGATATCT GTGGTAAGCA GTTCCTGCCC
4751  CGGCTCAGGG CCAAGAACAG ATGGAACAGC TGAATATGGG CCAAACAGGA
```

FIG. 5D

```
4801  TATCTGTGGT  AAGCAGTTCC  TGCCCCGGCT  CAGGGCCAAG  AACAGATGGT
4851  CCCCAGATGC  GGTCCAGCCC  TCAGCAGTTT  CTAGAGAACC  ATCAGATGTT
4901  TCCAGGGTGC  CCCAAGGACC  TGAAATGACC  CTGTGCCTTA  TTTGAACTAA
4951  CCAATCAGTT  CGCTTCTCGC  TTCTGTTCGC  GCGCTTCTGC  TCCCCGAGCT
5001  CAATAAAAGA  GCCCACAACC  CCTCACTCGG  GGCGCCAGTC  CTCCGATTGA
5051  CTGAGTCGCC  CGGGTACCCG  TGTATCCAAT  AAACCCTCTT  GCAGTTGCAT
5101  CCGACTTGTG  GTCTCGCTGT  TCCTTGGGAG  GGTCTCCTCT  GAGTGATTGA
5151  CTACCCGTCA  GCGGGGGTCT  TTCATT
```

FIG. 5E

RSV tar Rev M10 expression plasmid

| Region | From | To | Description |
|---|---|---|---|
| pBR322 | 1 | 36 | vector |
| enhancer | 37 | 610 | RSV |
| tar | 611 | 699 | tat responsive element |
| rev M10 | 700 | 1129 | Rev M10 orf |
| poly A | 1243 | | bov. GH |
| promoter | 1993 | 2300 | pSV neo |
| kana res. | 2346 | | pSV2 neo |
| poly A | 3360 | | pSV2 neo |
| pUC | 3459 | 5653 | plasmid ori/amp |

Rtrev. Seq  Length: 5653  April 8, 1993  14:30  Type: N  Check: 1915 ..

```
  1 GACGGATCGG GAGATCTCCC GATCCCCTAT GGTCGACTCT CAGTACAATC
 51 TGCTCTGATG CCGCATAGTT AAGCCAGTAT CTGCTCCCTG CTTGTGTGTT
101 GGAGGTCGCT GAGTAGTGCG CGAGCAAAAT TTAAGCTACA ACAAGGCAAG
151 GCTTGACCGA CAATTGCATG AAGAATCTGC TTAGGGTTAG GCGTTTTGCG
201 CTGCTTCGCG ATGTACGGGC CAGATATACG CGTATCTGAG GGGACTAGGG
251 TGTGTTTAGG CGAAAAGCGG GGCTTCGGTT GTACGCGGTT AGGAGTCCCC
301 TCAGGATATA GTAGTTTCGC TTTTGCATAG GGAGGGGGAA ATGTAGTCTT
351 ATGCAATACA CTTGTAGTCT TGCAACATGG TAACGATGAG TTAGCAACAT
401 GCCTTACAAG GAGAGAAAAA GCACCGTGCA TGCCGATTGG TGGAAGTAAG
451 GTGGTACGAT CGTGCCTTAT TAGGAAGGCA ACAGACAGGT CTGACATGGA
501 TTGGACGAAC CACTGAATTC CGCATTGCAG AGATAATTGT ATTTAAGTGC
551 CTAGCTCGAT ACAATAAACG CCATTTGACC ATTCACCACA TTGGTGTGCA
601 CCTCCAAGCT CTGCTTTTTG CCTGTACTGG GTCTCTCTGG TTAGACCAGA
651 TCTGAGCCTG GGAGCTCTCT GGCTAGCTAG GGAACCCACT GCTTAAGCTC
701 ATGGCAGGAA GAAGCGGAGA CAGCGACGAA GACCTCCTCA AGGCAGTCAG
```

FIG. 7A

```
 751  ACTCATCAAG TTTCTCTATC AAAGCAACCC ACCTCCCAAT CCCGAGGGGA
 801  CCCGACAGGC CCGAAGGAAT AGAAGAAGAA GGTGGAGAGA GAGACAGAGA
 851  CAGATCCATT CGATTAGTGA ACGGATCCTT AGCACTTATC TGGGACGATC
 901  TGCGAGCCTG TGCCTCTTCA GCTACCACCA GATCTGAGAC TTACTCTTGA
 951  TTGTAACGAG GATTGTGGAA CTTCTGGGAC GCAGGGGGTG GGAAGCCCTC
1001  AAATATTGGT GGAATCTCCT ACAGTATTGG AGTCAGGAAC TAAAGAATAG
1051  TGCTGTTAGC TTGCTCAATG CCACAGCTAT AGCAGTAGCT GAGGGGACAG
1101  ATAGGGTTAT AGAAGTAGTA CAAGAAGCTC TAGAGCTCGC TGATCAGCCT
1151  CGACTGTGCC TTCTAGTTGC CAGCCATCTG TTGTTTGCCC CTCCCCCGTG
1201  CCTTCCTTGA CCCTGGAAGG TGCCACTCCC ACTGTCCTTT CCTAATAAAA
1251  TGAGGAAATT GCATCGCATT GTCTGAGTAG GTGTCATTCT ATTCTGGGGG
1301  GTGGGGTGGG GCAGGACAGC AAGGGGGAGG ATTGGGAAGA CAATAGCAGG
1351  CATGCTGGGG ATGCGGTGGG CTCTATGGCT TCTGAGGCGG AAAGAACCAG
1401  CTGGGGCTCG AGGGGGGATC CCCACGCGCC CTGTAGCGGC GCATTAAGCG
1451  CGGCGGGTGT GGTGGTTACG CGCAGCGTGA CCGCTACACT TGCCAGCGCC
1501  CTAGCGCCCG CTCCTTTCGC TTTCTTCCCT TCCTTTCTCG CCACGTTCGC
1551  CGGCTTTCCC CGTCAAGCTC TAAATCGGGG CATCCCTTTA GGGTTCCGAT
1601  TTAGTGCTTT ACGGCACCTC GACCCCAAAA AACTTGATTA GGGTGATGGT
1651  TCACGTAGTG GGCCATCGCC CTGATAGACG GTTTTTCGCC CTTTGACGTT
1701  GGAGTCCACG TTCTTTAATA GTGGACTCTT GTTCCAAACT GGAACAACAC
1751  TCAACCCTAT CTCGGTCTAT TCTTTTGATT TATAAGGGAT TTTGGGGATT
1801  TCGGCCTATT GGTTAAAAAA TGAGCTGATT TAACAAAAAT TTAACGCGAA
1851  TTTTAACAAA ATATTAACGT TTACAATTTA AATATTTGCT TATACAATCT
1901  TCCTGTTTTT GGGGCTTTTC TGATTATCAA CCGGGGTGGG TACCGAGCTC
1951  GAATTCTGTG GAATGTGTGT CAGTTAGGGT GTGGAAAGTC CCCAGGCTCC
2001  CCAGGCAGGC AGAAGTATGC AAAGCATGCA TCTCAATTAG TCAGCAACCA
2051  GGTGTGGAAA GTCCCCAGGC TCCCCAGCAG GCAGAAGTAT GCAAAGCATG
```

FIG. 7B

```
2101  CATCTCAATT AGTCAGCAAC CATAGTCCCG CCCCTAACTC CGCCCATCCC
2151  GCCCCTAACT CCGCCCAGTT CCGCCCATTC TCCGCCCCAT GGCTGACTAA
2201  TTTTTTTTAT TTATGCAGAG GCCGAGGCCG CCTCGGCCTC TGAGCTATTC
2251  CAGAAGTAGT GAGGAGGCTT TTTTGGAGGC CTAGGCTTTT GCAAAAAGCT
2301  CCCGGGAGCT TGGATATCCA TTTTCGGATC TGATCAAGAG ACAGGATGAG
2351  GATCGTTTCG CATGATTGAA CAAGATGGAT TGCACGCAGG TTCTCCGGCC
2401  GCTTGGGTGG AGAGGCTATT CGGCTATGAC TGGGCACAAC AGACAATCGG
2451  CTGCTCTGAT GCCGCCGTGT TCCGGCTGTC AGCGCAGGGG CGCCCGGTTC
2501  TTTTTGTCAA GACCGACCTG TCCGGTGCCC TGAATGAACT GCAGGACGAG
2551  GCAGCGCGGC TATCGTGGCT GGCCACGACG GGCGTTCCTT GCGCAGCTGT
2601  GCTCGACGTT GTCACTGAAG CGGGAAGGGA CTGGCTGCTA TTGGGCGAAG
2651  TGCCGGGGCA GGATCTCCTG TCATCTCACC TTGCTCCTGC CGAGAAAGTA
2701  TCCATCATGG CTGATGCAAT GCGGCGGCTG CATACGCTTG ATCCGGCTAC
2751  CTGCCCATTC GACCACCAAG CGAAACATCG CATCGAGCGA GCACGTACTC
2801  GGATGGAAGC CGGTCTTGTC GATCAGGATG ATCTGGACGA AGAGCATCAG
2851  GGGCTCGCGC CAGCCGAACT GTTCGCCAGG CTCAAGGCGC GCATGCCCGA
2901  CGGCGAGGAT CTCGTCGTGA CCCATGGCGA TGCCTGCTTG CCGAATATCA
2951  TGGTGGAAAA TGGCCGCTTT TCTGGATTCA TCGACTGTGG CCGGCTGGGT
3001  GTGGCGGACC GCTATCAGGA CATAGCGTTG GCTACCCGTG ATATTGCTGA
3051  AGAGCTTGGC GGCGAATGGG CTGACCGCTT CCTCGTGCTT TACGGTATCG
3101  CCGCTCCCGA TTCGCAGCGC ATCGCCTTCT ATCGCCTTCT TGACGAGTTC
3151  TTCTGAGCGG GACTCTGGGG TTCGAAATGA CCGACCAAGC GACGCCCAAC
3201  CTGCCATCAC GAGATTTCGA TTCCACCGCC GCCTTCTATG AAAGGTTGGG
3251  CTTCGGAATC GTTTTCCGGG ACGCCGGCTG GATGATCCTC CAGCGCGGGG
3301  ATCTCATGCT GGAGTTCTTC GCCCACCCCA ACTTGTTTAT TGCAGCTTAT
3351  AATGGTTACA AATAAAGCAA TAGCATCACA AATTTCACAA ATAAAGCATT
3401  TTTTCACTG CATTCTAGTT GTGGTTTGTC CAAACTCATC AATGTATCTT
```

FIG. 7C

```
3451 ATCATGTCTG GATCCCGTCG ACCTCGAGAG CTTGGCGTAA TCATGGTCAT
3501 AGCTGTTTCC TGTGTGAAAT TGTTATCCGC TCACAATTCC ACACAACATA
3551 CGAGCCGGAA GCATAAAGTG TAAAGCCTGG GGTGCCTAAT GAGTGAGCTA
3601 ACTCACATTA ATTGCGTTGC GCTCACTGCC CGCTTTCCAG TCGGGAAACC
3651 TGTCGTGCCA GCTGCATTAA TGAATCGGCC AACGCGCGGG GAGAGGCGGT
3701 TTGCGTATTG GGCGCTCTTC CGCTTCCTCG CTCACTGACT CGCTGCGCTC
3751 GGTCGTTCGG CTGCGGCGAG CGGTATCAGC TCACTCAAAG GCGGTAATAC
3801 GGTTATCCAC AGAATCAGGG GATAACGCAG GAAAGAACAT GTGAGCAAAA
3851 GGCCAGCAAA AGGCCAGGAA CCGTAAAAAG GCCGCGTTGC TGGCGTTTTT
3901 CCATAGGCTC CGCCCCCCTG ACGAGCATCA CAAAAATCGA CGCTCAAGTC
3951 AGAGGTGGCG AAACCCGACA GGACTATAAA GATACCAGGC GTTTCCCCCT
4001 GGAAGCTCCC TCGTGCGCTC TCCTGTTCCG ACCCTGCCGC TTACCGGATA
4051 CCTGTCCGCC TTTCTCCCTT CGGGAAGCGT GGCGCTTTCT CAATGCTCAC
4101 GCTGTAGGTA TCTCAGTTCG GTGTAGGTCG TTCGCTCCAA GCTGGGCTGT
4151 GTGCACGAAC CCCCCGTTCA GCCCGACCGC TGCGCCTTAT CCGGTAACTA
4201 TCGTCTTGAG TCCAACCCGG TAAGACACGA CTTATCGCCA CTGGCAGCAG
4251 CCACTGGTAA CAGGATTAGC AGAGCGAGGT ATGTAGGCGG TGCTACAGAG
4301 TTCTTGAAGT GGTGGCCTAA CTACGGCTAC ACTAGAAGGA CAGTATTTGG
4351 TATCTGCGCT CTGCTGAAGC CAGTTACCTT CGGAAAAAGA GTTGGTAGCT
4401 CTTGATCCGG CAAACAAACC ACCGCTGGTA GCGGTGGTTT TTTTGTTTGC
4451 AAGCAGCAGA TTACGCGCAG AAAAAAAGGA TCTCAAGAAG ATCCTTTGAT
4501 CTTTTCTACG GGGTCTGACG CTCAGTGGAA CGAAAACTCA CGTTAAGGGA
4551 TTTTGGTCAT GAGATTATCA AAAAGGATCT TCACCTAGAT CCTTTTAAAT
4601 TAAAAATGAA GTTTTAAATC AATCTAAAGT ATATATGAGT AAACTTGGTC
4651 TGACAGTTAC CAATGCTTAA TCAGTGAGGC ACCTATCTCA GCGATCTGTC
4701 TATTTCGTTC ATCCATAGTT GCCTGACTCC CCGTCGTGTA GATAACTACG
4751 ATACGGGAGG GCTTACCATC TGGCCCCAGT GCTGCAATGA TACCGCGAGA
```

FIG. 7D

```
4801  CCCACGCTCA CCGGCTCCAG ATTTATCAGC AATAAACCAG CCAGCCGGAA
4851  GGGCCGAGCG CAGAAGTGGT CCTGCAACTT TATCCGCCTC CATCCAGTCT
4901  ATTAATTGTT GCCGGGAAGC TAGAGTAAGT AGTTCGCCAG TTAATAGTTT
4951  GCGCAACGTT GTTGCCATTG CTACAGGCAT CGTGGTGTCA CGCTCGTCGT
5001  TTGGTATGGC TTCATTCAGC TCCGGTTCCC AACGATCAAG GCGAGTTACA
5051  TGATCCCCCA TGTTGTGCAA AAAAGCGGTT AGCTCCTTCG GTCCTCCGAT
5101  CGTTGTCAGA AGTAAGTTGG CCGCAGTGTT ATCACTCATG GTTATGGCAG
5151  CACTGCATAA TTCTCTTACT GTCATGCCAT CCGTAAGATG CTTTTCTGTG
5201  ACTGGTGAGT ACTCAACCAA GTCATTCTGA GAATAGTGTA TGCGGCGACC
5251  GAGTTGCTCT TGCCCGGCGT CAATACGGGA TAATACCGCG CCACATAGCA
5301  GAACTTTAAA AGTGCTCATC ATTGGAAAAC GTTCTTCGGG GCGAAAACTC
5351  TCAAGGATCT TACCGCTGTT GAGATCCAGT TCGATGTAAC CCACTCGTGC
5401  ACCCAACTGA TCTTCAGCAT CTTTTACTTT CACCAGCGTT TCTGGGTGAG
5451  CAAAAACAGG AAGGCAAAAT GCCGCAAAAA AGGGAATAAG GGCGACACGG
5501  AAATGTTGAA TACTCATACT CTTCCTTTTT CAATATTATT GAAGCATTTA
5551  TCAGGGTTAT TGTCTCATGA GCGGATACAT ATTTGAATGT ATTTAGAAAA
5601  ATAAACAAAT AGGGGTTCCG CGCACATTTC CCCGAAAAGT GCCACCTGAC
5651  GTC
```

RECOMBINANT NUCLEIC ACIDS FOR INHIBITING HIV GENE EXPRESSION

BACKGROUND OF THE INVENTION

Infection by the human immunodeficiency virus (HIV) leads to the progressive depletion of CD4+ T cells which causes Acquired Immunodeficiency Syndrome (AIDS). Infection by the human immunodeficiency virus is typically characterized by an asymptomatic, or latent, phase of the disease. During this time, infected persons may not exhibit signs of immunodeficiency. Nonetheless, these asymptomatic, seropositive individuals synthesize virus which progressively depletes CD4+ T cells and which is infectious.

It is currently estimated that there are over one million seropositive cases with latent HIV infection in the United States today. These individuals, for whom there are no known effective treatments, are likely to progress and succumb to this disease. Therefore, a major therapeutic goal is to prolong the latent phase of HIV infection.

We have previously shown that activation of HIV gene expression is controlled by a cellular transcription factor, NF-κB (1). This transcription factor is inactive in resting T cells but is stimulated following cell activation and induces viral transcription. In addition to NF-κB, there are essential viral genes which also appear to regulate the transition from latent to active infection.

An important viral regulatory protein in HIV gene expression is Rev, an 18 kilodalton (kD) nuclear protein which controls export of viral RNA from the nucleus to the cytoplasm of infected cells. In contrast to NF-κB, the Rev protein is unique to HIV and thus unlikely to regulate essential cellular functions.

Viral replication is critically dependent on the interaction of viral gene products with host cell factors. Because viruses are intimately associated with their host cells, it has been difficult to selectively interfere with replication in vivo. Successful anti-viral approaches have selectively targeted viral gene products. For example, the treatment of herpes simplex virus (HSV) infection has taken advantage of the ability of a viral gene, thymidine kinase, to modify a drug which is toxic to the host cell. This approach led to the development of guanosine analogues, including acyclovir and ganciclovir (2–4), which are converted to DNA chain terminators only in HSV infected cells.

In HIV infection, traditional pharmaceutic targeting has thus far provided limited benefits. Although AZT has relative selectivity for viral reverse transcriptase, its toxic effect on host cell function and its low therapeutic index have provided limited protection against the progression of AIDS.

More recently, as molecular biologic studies have advanced, it has become possible to use recombinant genes to interfere with HIV gene expression. Several promising approaches have been used to exploit gene transfer to inhibit viral replication, including antisense RNA (5–7), catalytic RNA (ribozymes) (8–11), and RNA analogs or decoys (12). Viral proteins also can serve as targets for inhibition by recombinant gene products. These are well-known and contain domains which can be characterized with respect to structure and function.

Recent success in protecting cells from HIV infection using TAR analogs has provided evidence that it is possible to render cells resistant to HIV infection (12) through recombinant gene products.

The concept of dominant negative inhibition was initially described in yeast genetic systems (13). It was subsequently demonstrated that anti-viral effects could be conferred on cells susceptible to infection by herpesvirus. Using the herpesvirus VP16 transactivator, mutant proteins lacking the transactivation domain of this protein were generated which could interfere with viral replication (14).

There exists a need in the art for improved means and methods to interfere with HIV gene expression.

SUMMARY OF THE INVENTION

This invention provides recombinant nucleic acid molecules and vectors for the improved expression of genes which inhibit HIV gene expression. This invention also provides methods for inhibiting HIV gene expression and methods for treating HIV infection.

More particularly, this invention provides recombinant nucleic acid molecules having a high level expression control sequence and a TAR sequence, operatively linked to a protective gene. The Rous Sarcoma Virus (RSV) promoter is a high level expression control sequence useful in this invention.

The protective genes of this invention include those genes whose expression inhibits the expression of HIV genes. Protective genes include negative transdominant mutant genes of HIV genes, including mutants of the rev and gag genes and, in particular, Rev M10. They also include functional nucleic acids, such as ribozymes, antisense nucleic acids and decoy nucleic acids that inhibit the expression of HIV genes.

This invention also provides plasmid and retroviral vectors having the recombinant nucleic acid molecules of this invention inserted therein for transfecting cells susceptible to HIV infection. In particular, this invention provides RSV tar Rev M10 expression plasmid.

This invention also provides transfected cells having the recombinant nucleic acid molecules of this invention. In particular, this invention provides transfected T cells, hematopoietic stem cells, monocytes, macrophages, dendritic cells and neuronal cells.

This invention also provides methods of inhibiting HIV gene expression in a cell by transfecting a cell with a recombinant nucleic acid molecule of this invention.

This invention also provides methods of treating HIV infection by introducing into an individual infected with HIV a transfected cell which comprises a recombinant nucleic acid molecule of this invention.

BRIEF DESCRIPTION OF THE DRAWINGS

FIGS. 4-A to 4-E (SEQ ID NO: 1) depict the nucleotide sequence of pLJ Rev m10 retroviral vector.

FIGS. 5-A to 5-E (SEQ ID NO: 2) depict the nucleotide sequence of pLJ mutant Rev m10 retroviral vector.

FIGS. 7-A to 7-E (SEQ ID NO: 3) depict the nucleotide sequence of RSV tar Rev M10 expression plasmid.

DETAILED DESCRIPTION OF THE INVENTION

Figure 1:
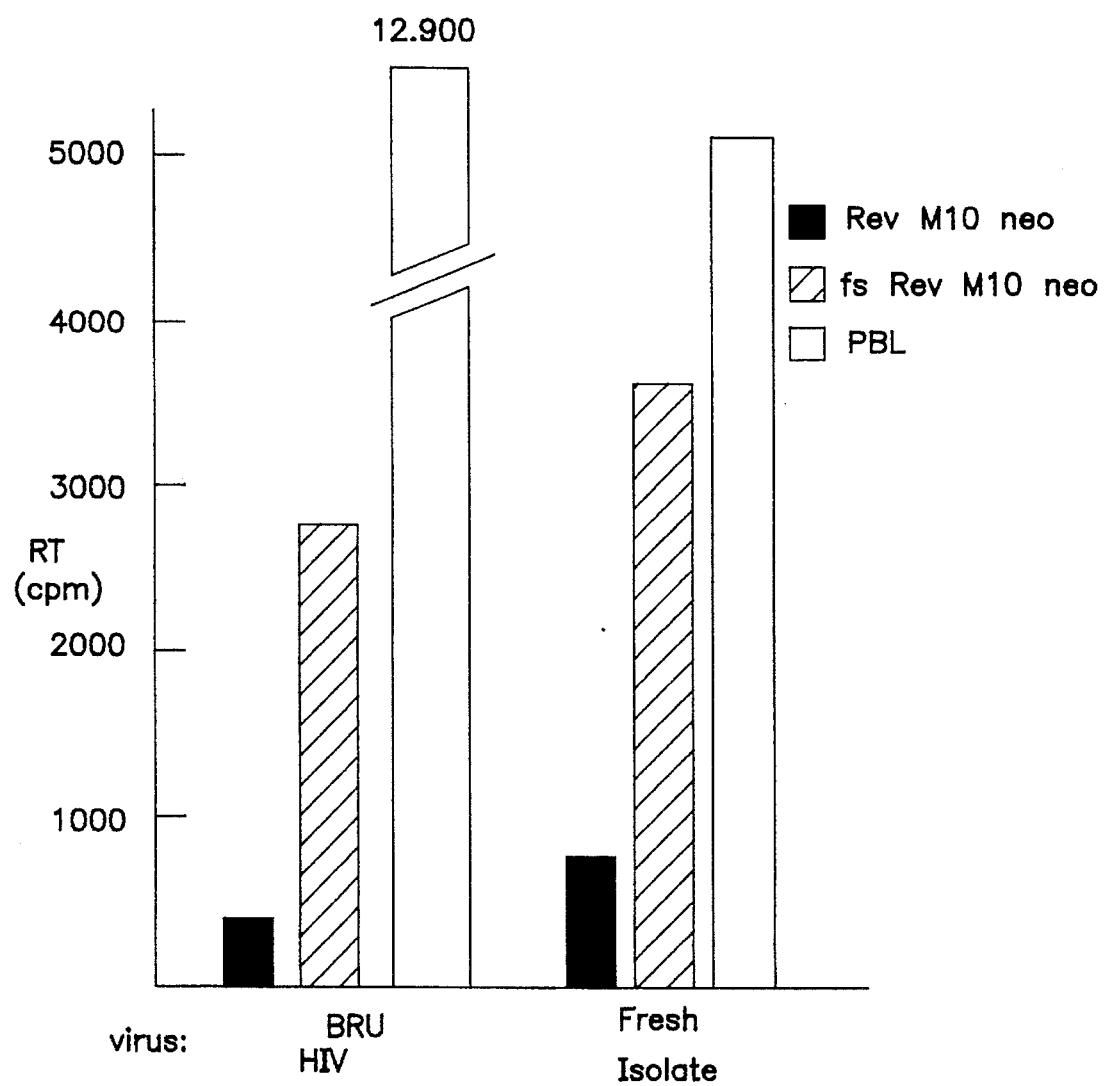
FIG. 1 depicts the level of reverse transcriptase (RT) activity in human T cells transfected with retroviruses containing Rev M10 neo, Rev M10 neo frameshift or in untransduced peripheral blood lymphocytes.

The expression of HIV genes can be inhibited by the expression of the negative transdominant gene Rev M10 (31). In particular, expression systems in which Rev M10 is under the transcriptional and translational control of a high level constitutive expression control sequence and a TAR sequence show markedly improved ability to inhibit HIV gene expression in HIV-infected T cells compared to Rev M10 under the control of either a high level constitutive expression control sequence, alone, or a TAR sequence expressed with a weak expression control sequence, for example, the HIV LTR. This discovery holds promise for both the inhibition of HIV gene expression in cells and for the treatment of persons infected with HIV.

The practice of this invention involves the use of molecular cloning techniques well known in the art. Examples of these techniques are described in, for example, Sambrook et al. (26).

This invention provides recombinant nucleic acid molecules comprising a high level expression control sequence and a TAR sequence, operatively linked to a protective gene.

As used herein, the term "recombinant nucleic acid molecule" refers to a recombinant DNA molecule or a recombinant RNA molecule. A recombinant nucleic acid molecule is any nucleic acid molecule containing joined nucleic acid molecules from different original sources and not naturally attached together. Recombinant RNA molecules include RNA molecules transcribed from recombinant DNA molecules. In particular, recombinant RNA molecules include the RNA molecules of a retroviral vector.

As used herein, the term "expression control sequence" refers to a nucleic acid sequence that regulates the transcription and translation of a gene to which it is operatively linked. An expression control sequence is "operatively linked" to a gene when the expression control sequence controls and regulates the transcription and, where appropriate, translation of the gene. The term "operatively linked" includes the provision of an appropriate start codon (e.g. ATG), in front of a polypeptide-encoding gene and maintaining the correct reading frame of that gene to permit proper translation of the mRNA.

By the term "high level" expression control sequence, we mean an expression control sequence which, when operatively linked to a gene and transfected into the Jurkat T cell leukemia cell line, results in a level of expression of that gene that is least five-fold higher than that caused by the HIV LTR operatively linked to the same gene. The level of expression of an expression control sequence can be determined empirically.

Constitutive expression control sequences are particularly useful in this invention. Inducible expression control sequences which, upon induction, exhibit levels of expression similar to the high level constitutive expression control sequences of this invention are also useful.

The Rous Sarcoma Virus ("RSV") promoter finds use in this invention as a high level expression control sequence. The RSV promoter is commonly used in the art for the expression of recombinant nucleic acid molecules (32). Nucleotides 37–610 of FIG. 7 (SEQ ID NO: 3) encodes an RSV promoter useful in this invention.

Other high level expression control sequences can be constructed by combining promoter and enhancer elements. Useful promoters include those which can promote expression of a gene in the cell to be transfected. For example, the β-actin promoter functions in many cell lines. Enhancer regions useful in this invention are those enhancers demonstrating a high level of expression in combination with a constitutive promoter. For example, the CMV enhancer, the CD4 locus control region enhancer, or any enhancer having at least four κB sites find use in this invention. One useful property of the CD4 locus control region enhancer is that, if used to transfect hematopoietic stem cells, it will enhance expression of genes in cells that, as a result of differentiation, express CD4. Other enhancers providing high levels of constitutive expression can be identified empirically.

Examples of constructed high level expression control sequences include the CMV enhancer fused to the β-actin promoter, the CD4 locus control region enhancer fused to the β-actin promoter, and at least four κB sites fused to the β-actin promoter.

The recombinant nucleic acid molecules of this invention include a TAR sequence located downstream (i.e. 3' relative to) the expression control sequence. The TAR sequence is a nucleic acid sequence found in the HIV genome. The regulatory activity of the tat protein depends on the TAR sequence. In this invention, the TAR sequence is also operatively linked to, and therefore controls the expression of, the protective gene. TAR sequences useful in this invention include, for example, the sequence of nucleotides 611–699 from FIG. 7 (SEQ ID NO: 3). They also include other TAR sequences know to the art, such as:

```
5' GGGGTCTCTC TGGTTAGACC AGATCTGAGC CTGGGAGCTC
TCTGGCTAAC TAGGGAACCC ACG 3' (SEQ ID NO: 4)
(Refs. 30 and 31).
```

The TAR sequences of this invention also include TAR sequences from various strains of HIV or other viruses that hybridize to the TAR sequence of nucleotides 611–699 of FIG. 7 (SEQ ID NO: 3) under stringent conditions and upon which tat protein activity depends.

A recombinant nucleic acid molecule finding use in this invention comprises the RSV promoter and the TAR sequence of FIG. 7, nucleotides 37–699 of SEQ ID NO: 3.

As used herein, the term "protective gene" refers to any gene whose expression inhibits expression of an HIV gene and, consequently, interferes with replication of the HIV virus. Negative transdominant genes and genes encoding functional nucleic acids find use as protective genes in this invention.

Negative transdominant genes include those mutant forms of a wild-type gene which, when introduced into a cell expressing the wild type gene, interfere with the expression of the wild type phenotype. Negative transdominant genes useful in this invention include mutant form of rev, gag, tat, nef, vpx, integrase, and reverse transcriptase.

In one embodiment of this invention, the protective gene is a negative transdominant rev mutant. In particular, we have used the Rev M10 mutant. The nucleic acid sequence of Rev M10 is provided in nucleotides 700–1129 of FIG. 7 (SEQ ID NO: 3).

As used herein, the term "functional nucleic acid" is any nucleic acid which, upon transcription, exhibits enzymatic function or regulates the translation of an mRNA so as to interfere with the expression of an HIV gene. Functional nucleic acids include ribozymes or antisense nucleic acids. Ribozymes useful in this invention are those that cleave HIV gene transcripts. Antisense molecules useful in this invention are those that hybridize to HIV gene transcripts. Functional nucleic acids also include decoy nucleic acids. A decoy nucleic acid is a nucleic acid which binds to an HIV regulatory protein, such as tat or rev. Useful decoy nucleic acid sequences include the TAR sequence (which regulates tat) and the HIV RRE sequence (which regulates rev).

In one embodiment of the invention, the recombinant nucleic acid molecule includes the RSV promoter and a TAR sequence, operatively linked to the Rev M10 transdominant mutant. One embodiment of this construct comprises nucleotides 37–610, nucleotides 611–699, and nucleotides 700–1129 of FIG. 7 (SEQ ID NO: 3). Another embodiment of this invention comprises nucleotides 37–1129 of FIG. 7 (SEQ ID NO: 3).

According to other embodiments of this invention, the expression control sequence includes a translational enhancer. We used an encephalomyocarditis virus internal ribosome entry site. The recombinant nucleic acid molecule of this invention may also include an mRNA stability enhancer.

The recombinant nucleic acid molecules of this invention find use, among other things, for the high level expression of protective genes which may then be recovered.

This invention also provides vectors comprising the recombinant nucleic acid molecules of this invention. These include plasmid vectors, viral vectors and liposomes. Viral vectors include retroviral vectors or adeno-associated viral vectors, having inserted therein the recombinant nucleic acid molecules of this invention for transfecting cells susceptible to HIV infection. Plasmid vectors include those functioning in the target cells of this invention. In particular, this invention provides RSV tar Rev M10 expression plasmid.

This invention also provides stably transfected cells having the recombinant nucleic acid molecules of this invention. Cells most useful as hosts in this invention are those cells which are infectable by HIV, for example, $CD4^+$ T cells, or their progenitors, for example, hematopoietic stem cells, as well as monocytes, macrophages, dendritic cells and neuronal cells. The transfected cells of this invention include both those already infected with HIV, and those uninfected. Also included are progeny cells of the transfected cells. These progeny cells stably express the protective gene. As used herein "transfected" or "transfection" means insertion of the vector into a host cell by methods well known in the art. See Sambrook et al. supra.

This invention further provides a method of producing a polypeptide comprising culturing the transfected cells described above under conditions permitting transcription of the protective gene into RNA and translation of the RNA into a polypeptide.

This invention also provides methods of inhibiting HIV gene expression in a cell by transfecting a cell with the recombinant nucleic acid of this invention. Host cells can be transfected by any methods known to the art. For example, methods for retroviral transfection are described in, for example, M. Krieger (33) and *Methods in Enzymology*, Vol. 185 (34). Cells can be transfected with plasmid vectors, for example, by electroporation. Cells can be transfected by recombinant nucleic acid molecules by calcium phosphate precipitation DNA liposome complexes or by particle-mediated gene transfer (biolistics). Methods are also known for transfection of nucleic acids using liposomes.

This invention also provides a method of treating an individual subject infected with HIV, which comprises administering to the individual a vector as described hereinabove. Suitable methods of administering the vector in pharmaceutical form are well known to those of ordinary skill in the art, and include, but are not limited to, administration of the vector in a pharmaceutically acceptable carrier. Suitable methods of administration include, but are not limited to, administration orally, intravenously or parenterally. Administration of the vector must be in dose and in such a form such that the vector is transduced into the cell, so that the protective gene is transcribed in an amount effective to inhibit HIV gene expression.

A method of intracellularly immunizing an individual against HIV infection is also provided which comprises removing hematopoietic stem cells from the patient and infecting the removed stem cells with an effective amount of a vector described hereinabove. The infected cells are then administered back into the patient, i.e., into the patient's bone marrow, thereby intracellularly immunizing the patient against HIV infection. For the purposes of this invention, intracellular immunization means prophylaxis as well as treatment of an infection.

EXAMPLE I

RECOMBINANT NUCLEIC ACID MOLECULES WITH HIGH LEVEL EXPRESSION CONTROL SEQUENCE AND TAR

A. Rev M10 and mutant Rev M10

Figure 6:
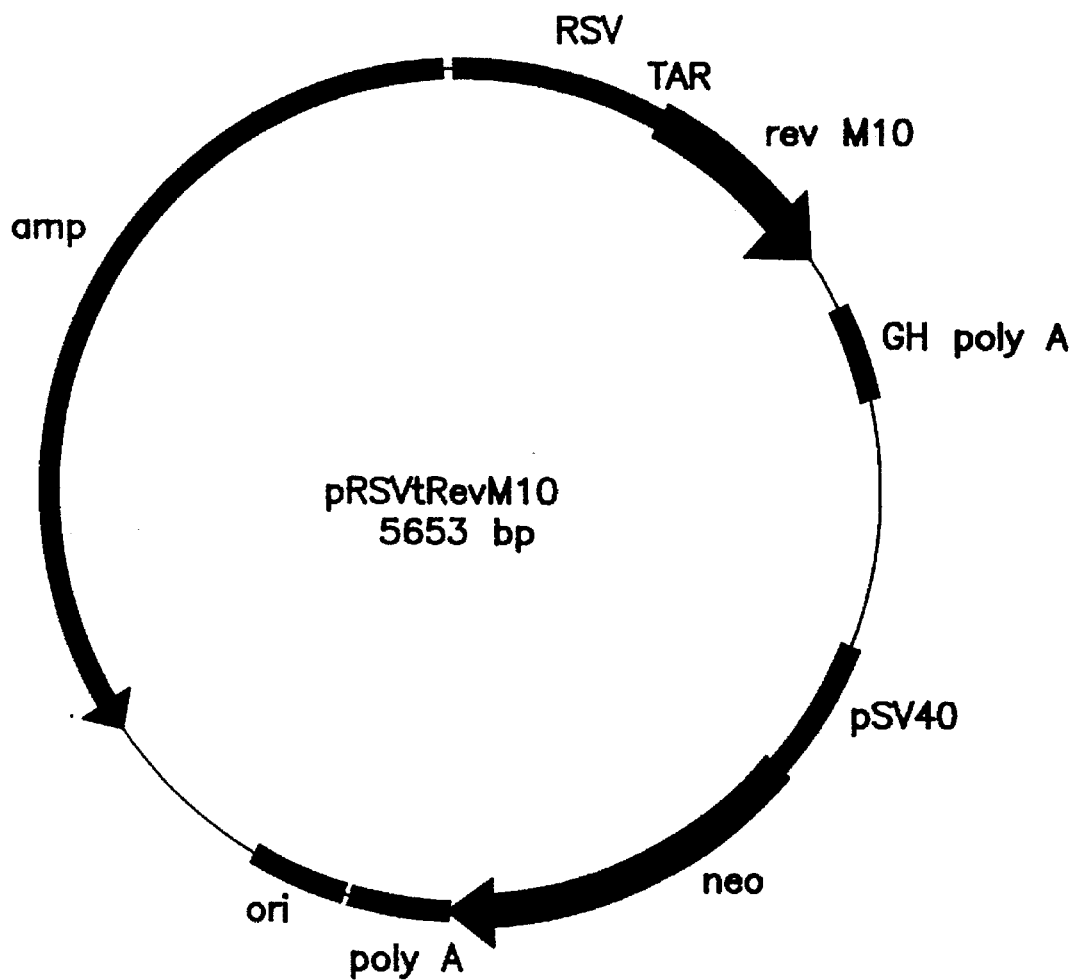
FIG. 6 depicts RSV tar Rev M10 expression plasmid.

The RSV-tar Rev M10 plasmid (FIG. 6) was prepared as follows. Plasmid pRSV-ADH (32) (kindly provided by Drs. Wen-Chang Lin and Lloyd Culp, Case Western Reserve University) was digested with HindIII and XbaI, incubated with Klenow enzyme and ligated to an insert. The insert was derived by digestion of the CMV Rev M10 plasmid (pBC12-CMV cRev M10 (ref. 16)) with NcoI and HindIII treated with Klenow which had previously been blunt end ligated to the pvuII to HindIII region of the HIV-1 LTR derived from HIV-CAT (1). HIV-CAT contains TAR, the tat target region. The resulting plasmid expresses the Rev M10 protein from the RSV enhancer linked to a TAR sequence and having a bovine growth hormone polyadenylation sequence. The G418 resistance gene is included downstream from the sv40 early region promoter. The nucleic acid sequence of RSV tar Rev M10 is given in FIG. 7 (SEQ ID NO: 3).

The upstream PCR primer to detect this vector includes bp 688–707:

5' ACTGCTTAAG CTCATGGCAG 3' (SEQ ID NO: 5).

The mutant Rev M10 vector was created by site-directed mutagenesis to delete nucleotides 700–702 and C to G at position 689. The upstream PCR primer extends from position 679 to 703:

5' AGGGAACCCA GTGCTTAAGC TTG 3' (SEQ ID NO: 6).

The sequence is otherwise identical to the RSV-tar Rev m10 vector.

The Rev M10 gene is introduced into $CD4^+$ cells after removal of $CD8^+$ cells with antibody-coated plates (see Example IV).

EXAMPLE II

RECOMBINANT NUCLEIC ACID MOLECULES WITHOUT TAR

A. Structure of retroviral vectors which express Rev M10 or ΔRev10

1. Vector

The parental vector has been described in a previous publication (28). The basic structure of these vectors is briefly described here. The background of this vector includes an intact 5' LTR of Moloney murine leukemia virus (Mo-MLV) with additional Mo-MLV sequences between the 5' LTR and the internal promoter spanning nucleotide 146 at the border of U5 to 1031 and the vector contains SV40-neo sequences linked to the pBR322 ori, followed by Mo-MuLV (nt 7188–7815) followed by the 3' LTR (nt 7816–8264, 1–145).

2. Rev M10

The coding sequence for Rev M10 was derived from a 0.5 kb NcoI to XhoI fragment CMV/IN-Rev M10 (16), which contains a 5' initiation codon ATG and 3' untranslated region and has been shown to express very highly in several different expression vectors. The NeoI site was blunted and ligated into the blunted BamHI to SalI site poly linker at position 1037 in the parental vector, PLJ. The resulting plasmid is called pLJ Rev m10 retroviral vector. The nucleotide sequence of pLJ Rev m10 retroviral vector is provided in FIG. 4 (SEQ ID NO: 1).

A primer has been made to detect this sequence:

5' CGTTCTGTGT TGGATCCCAT GGCAGG 3' (SEQ ID NO: 7)

at nt 1021–1046. The same downstream reverse complement primer is used for all vectors and can distinguish between wild type Rev and Rev M10.

3. ΔRev M10

For the control, we have synthesized a mutant plasmid with a deletion of 5' AUG codon of M10 coding sequence. The PLJ-ΔRev M10 is identical to PLJ-Rev M10 except that the ATG of the initiating methionine in the coding sequence was removed with $S_1$ nuclease and additional 65 nucleotides of the 5' untranslated region of pre-proinsulin was inserted. The nucleotide sequence of pLJ mutant Rev m10 is provided in FIG. 5 (SEQ ID NO: 2).

An upstream primer has been made to amplify this unique vector sequence:

5' GTTTAGTAAG TCAAGCTTAA GTG 3' (SEQ ID NO: 8)

at nt 1043–1065. The junction sequence of this plasmid was confirmed by dideoxy sequencing.

4. Summary

In summary, the Rev M10 gene produces an RNA transcript which encodes a dominant negative mutant form of Rev by substituting Asp Leu for Leu Glu at positions 78 and 79. The second vector, ΔRev M10, is identical to the first except that Rev M10 protein is not synthesized, but can be distinguished from the Rev M10 vector by PCR. Thus, nearly identical transcripts are generated by each vector except that Rev M10 protein is not synthesized in the control ΔRev M10 vector. The plasmid DNA is grown in a standard *E. coli* host strain (DH 5α or XL1-Blue) and introduced into the ψCRIP packaging line by standard techniques.

B. Generation of Retroviral Vectors Encoding Rev M10 or ΔRev M10

Viral-producing cell lines were isolated for each vector using the amphotropic packaging cell line ψ-Crip (29). Briefly, ψ-Crip cell line was generated by transfecting the gag-pol and env functions on separate plasmids into NIH 3T3 cells. The 3' LTRs of the constructs were replaced with heterologous polyadenylation sequences. These modifications were performed to minimize the chance that recombination could result in the production of replication competent virus.

The vectors were transfected into ψ-Crip, and stably transfected clones were selected in G418 (1 mg/ml). Individual clones (25 from each transfection) were isolated and analyzed for production of virus. The producer is maintained in Dulbecco's modified medium supplemented with 10% bovine calf serum and 1% penicillin/streptomycin. Supernatants from confluent plates of clones were harvested and exposed to subconfluent plates of 3T3 cells in the presence of polybrene (8 μg/ml). Expression of Rev M10 and ΔRev M10 mRNA is confirmed by reverse transcription PCR and by immunoprecipitation of internally labeled cellular proteins. A substantial activity is found in a sub-population of fibroblasts from each infected culture: the relative size of this sub-population, which is an indication of the efficiency of gene transfer and expression, ranged from 20% to 50% of all cells for PLJ-Rev M10 or PLJ-ΔRev M10. Virus-producing cell lines were maintained in culture for 4–6 weeks prior to their use in order to test for the development of helper virus.

C. Transfection of cells

Freshly isolated viral supernatants were analyzed for replication competent virus using the previously described LacZ mobilization assay. NIH 3T3 cells harboring a single copy of a recombinant retroviral genome encoding *E. coli* β-galactosidase were exposed to the viral supernatant and maintained in culture for 7–10 days. A supernatant was harvested and used to infect NIH 3T3 cells which were subsequently analyzed for LacZ expressing cells using X-gal chromogenic assay. None of the virus producers have scored positive for replication competent virus or packaging of the packaging genome using this sensitive assay.

EXAMPLE III

RETROVIRAL VECTORS FOR HIGH LEVEL EXPRESSION OF PROTECTIVE GENES

Retroviruses containing the recombinant nucleic acid molecules of this invention also can be constructed. In this case, a retrovirus is provided with a recombinant nucleic acid molecule encoding an expression control sequence and a TAR sequence, operatively linked to a protective gene.

Such retroviral vectors may be produced using the retroviral vectors described in Example II. To construct such retroviral vectors, the sequences encoding the expression control sequences and protective genes of pLJ Rev m10 retroviral vector are removed and replaced with a nucleic acid sequence of this invention. For example, nucleotides 1–449 of FIG. 4 (SEQ ID NO: 1) are removed and replaced with nucleotides 37 to 1129 of FIG. 7 (SEQ ID NO: 3).

EXAMPLE IV

METHODS

A. Selection of $CD4^+$ cells

AIS CELLector™ CD8 Cell Culture Flasks consist of a polystyrene tissue culture flask with murine CD8 monoclonal antibodies covalently bonded to the polystyrene surface of the flask (Applied Immune Sciences, Inc., Menlo Park, Calif.). The adherence of the antibodies to the flask surface remains stable throughout the cell separation procedure. The CELLector™ CD8 Cell Culture Flask selects CD8(+) T-cells from peripheral mononuclear cells (PMBC) or cultured lymphocytes. The CELLector™ CD8 Cell Culture Flask depletes CD8(+) cell preparations. The flask is terminally sterilized; therefore, CD8 cell separation occurs within a protective and sterile environment. The remaining cells are >90% enriched for CD4$^+$ T cells. Each flask (150 cm$^2$) is loaded with 30 ml of 2–3×10$^6$ cells ml. The flask is incubated for 1 hour at room temperature. Non-adherent cells are removed, and cultured in AIM V media and stimulated as indicated below. Cellular phenotype is assessed by flow cytometry prior to study.

B. Primary Anti-CD3 Activation

For primary anti-CD3 activation, 3–4×10$^8$ lymphocytes are suspended in 70 ml of complete media (CM) and cultured in 175 cm$^2$ flasks with immobilized OKT 3 mAB. Flasks are coated with mAB by adding 10–20 ml of diluted OKT 3 (1 µg/ml) in sterile 0.05M borate buffer, pH 8.6, and stored at 4° C. Prior to use, the flask is washed extensively of excess mAB with HBSS. CM is composed of RPMI 1640 (GIBCO or MA Bioproducts) with 10% human AB serum (GIBCO or Whittacker), 2 mM glutamine, and 50 µg/ml gentamicin. After 2 days of activation, the cells are harvested, washed, and expanded in IL-2.

Expansion in IL-2 is accomplished by resuspending 1–2 ×10$^5$ anti-CD3 activated cells/ml in fresh CM containing 60 IU/ml of IL-2 (Cetus, Emeryville, Calif.). These cells are expanded in 3000 ml culture bags (Lifecell PL732, Fenwal, Deerfield, Ill.) each containing 500–1000 ml of media. Cells are grown to maximum density (~1–2×10$^6$ cells/ml) which is anticipated to take 3–4 days based on our preliminary experience.

C. Harvesting Conditions

One out of ten bags is tested for sterility 48 hours before harvesting by obtaining an aliquot of cells and sending it for culture by the Microbiology Laboratory of the University Hospital. Bacterial monitoring includes thioglycolate broth, chocolate agar, and sheeps' blood agar. Cell suspensions from the culture bags are harvested and washed in phenol-free HBSS using the Celltrifuge II (Fenwal). For infusion, the cells are suspended in 200 ml saline containing 1.25% human albumin and 450,000 IU Il–2. A gram stain of the final cell pellet is evaluated to confirm that there are no organisms prior to infusion.

D. PCR Analysis

Ten-fold dilutions of cells are introduced into 2×10$^6$ peripheral blood lymphocytes (PBL) from an uninfected individual. Standards are prepared by diluting CEM cells, of which 100% contain the Rev M10 or ΔRev M10 gene. Chromosomal DNA is prepared from these cells by lysing them in 1% SDS, 200 µg/ml proteinase K, 100 mM NaCl 100 mM TrisHCl and 25 mM EDTA at 55° C. for 16 hours. Cell lysis was followed by phenol/chloroform/isoamyl alcohol (25:24:1) extraction and ethyl alcohol precipitation (26). One microgram of DNA is amplified by PCR in a total volume of 50 µl, which contained 0.2 mM of deoxynucleoside triphosphatases, 1 µM of 5' and 3' oligonucleotide primers, 50mM KCl mM Tris-Cl, pH 8.3, 1.5mM MgCl$_2$, and 2.5 units of Taq polymerase. PCR is performed in a DNA thermal cycler (Perkin-Elmer, Norwalk, Conn.). The amplification cycle consists of 28 cycles of denaturing at 94° C. for 1 minute, annealing of primers at 60° C. for 2 minutes, and extension at 72° C. for 2 minutes (27). In the initial cycle, the DNA is denatured for 1.5 minutes. The final cycle includes a 10-minute elongation process. The nucleotide sequences for Rev M10 and ΔRev M10 are used to generate the oligonucleotide primers for PCR. The amplified products are separated on 1% agarose gels, transferred to membranes, hybridized with the $^{32}$P-labeled internal Rev probe, and developed by autoradiography on Kodak XAR film at −70° C. (26).

E. Testing of Retroviral Supernatants

The following tests is performed on Rev M10 and ΔRev M10 supernatants: a. titre, b. sterility, c. Map test, d. Leu virus, e. thymic agent, f. S$^+$/L$^-$ for ecotropic virus, g. S$^+$/L$^-$ for xenotropic virus, h. S$^+$/L$^-$ for amphotropic virus, i. 3T3 amplification by standard methods.

F. Transduction of CD4(+) PBL

Frozen Rev M10 and ΔRev M10 supernatants are stored at −70° C. On the day of transduction, aliquots are thawed and passed through Corning 0.45 micron filters. Cells are resuspended at a concentration of 10$^6$ ml in a transduction mixture consisting of 50% AIM V+1000 µ/ml IL-2 and 50% viral supernatant (an infectivity ratio of 2–3:1) supplemented with protamine sulfate at a final concentration of 5 µg/ml. After incubation at 37° C. for 4 hours, cells are washed 3 times in AIMV and introduced into tissue culture bags for large scale expansion of cells for therapy. CD4(+) PBL is prepared as described above. These cells are cultured in T150 flasks.

G. Tests on Transduced CD4$^+$ Populations a. Viability—greater than 70% by trypan blue exclusion.
b. Cytology—prior to infusion, a cytologic analysis is performed on Cytospin preps to assure that no tumor cells are present.
c. Sterility—cultures are analyzed by Gram stain and cultured for aerobic and anaerobic bacteria, fungus, and mycoplasma, although cultures will not always be possible prior to re-infusion.
d. S$^+$/L$^-$ assay—negative including 3T3 amplification.
e. Phenotype—flow cytometric analysis is performed using the following panel of antibodies: CD3/CD8, CD3/CD4.
f. mRNA expression—whole cellular RNA is extracted from cells and RNA expression confirmed by RT-PCR using limiting dilution.
g. An aliquot of these cells is maintained and challenged in vitro for infection by HIV.

H. Transduction of cells by particle-mediated gene transfer

CD4$^+$ human peripheral blood T cells were isolated from Ficoll-Hypaque-purified leukocytes by standard methods. After storage on ice overnight, cells underwent particle-mediated gene transfer with DNA-coated gold beads using an ACCELL™ device (Agracetus). Average gold bead diameter was 0.95µ. The DNA vector containing the gene of interest, trans-dominant M10 mutant of the HIV rev gene (revM10) under the control of various promoters, including RSV-tar, were used.

RevM10-containing vectors were linearized by cutting with the AatII restriction endonuclease, which makes a single cut in the beta lactamase (ampicillin resistance) gene. Vectors were then precipitated onto the gold beads at 2.5 µg DNA per mg of gold. After resuspension in 100% ethanol, the DNA-coated gold was layered onto mylar sheets (1.8× 1.8 cm) at 0.1 mg gold per cm$^2$. Thus, each sheet had 810 ng of DNA.

CD4 cells in aliquots of 5×10$^5$ cells were treated with the gold-coated sheets described above. In the ACCELL™ device, the gold-coated mylar sheets are propelled against a screen by the force of expansion of a water droplet that has had an electrical current passed through it. The mylar sheet is stopped by the screen, and the DNA-coated gold beads continue through the screen into the target cells or tissue at a voltage of 5.5 kV.

Cells treated with DNA-coated gold in this way were pooled and plated at various concentrations ($2\times10^4$ to $2\times10^2$/well in 96-well microtiter plates) and stimulated with phytohemagglutinin (Difco Leukagglutinin, 5 µg/ml), or anti-CD3, and human IL-2 at 50 U/ml. Selection with G418 (100 µg/ml of active G418) was begun 3 days later.

Positive control plates received the same stimuli, and G418 was not added. Negative control plates did receive G418 selection, but did not receive any vector, and so did not receive the neo gene. No clones grew in these negative control plates; i.e., the non-transfected cells did not establish visible clones in the presence of G418. Frequencies of Rev M10 G418 resistant clones were estimated to 0.1% of cells.

The cells which are modified by direct gene transfer in vivo include peripheral blood lymphocytes, including T lymphocytes and mononuclear cells. The transfer of the recombinant DNA is intended to prevent productive viral replication in these cells by acting as intracellular inhibitors which prevent the action of Rev, an essential viral gene. This effect cannot be achieved in any other way.

V. RESULTS

Freshly isolated PBMC's were stimulated for 48 hours at 37° C. with 5 µg/ml PHA. On day 3 and 5, cells were infected for 8 hrs with ψcrip supernatants, (plus 5 µg/ml polybrene) containing the PLJ-Rev M10 neo or frameshift PLJ-fs Rev M10(neo) retrovirus. Cells were subsequently selected with 300 µg/ml G418 for a further 8 days. On day 8, $5\times10^6$ cells in 0.5 ml of medium were incubated with approximately $5\times10^4$ $TCID_{50}$ of $HIV^{bru}$ or a freshly passaged clinical isolate for 2 hrs at 37° C. Cells were washed and re-suspended at $1\times10^6$/ ml. Day 7 post HIV infection, duplicate culture supernatants (10 µl) were assayed for reverse transcriptase (RT) activity. The results are depicted in FIG. 1.

Figure 2:
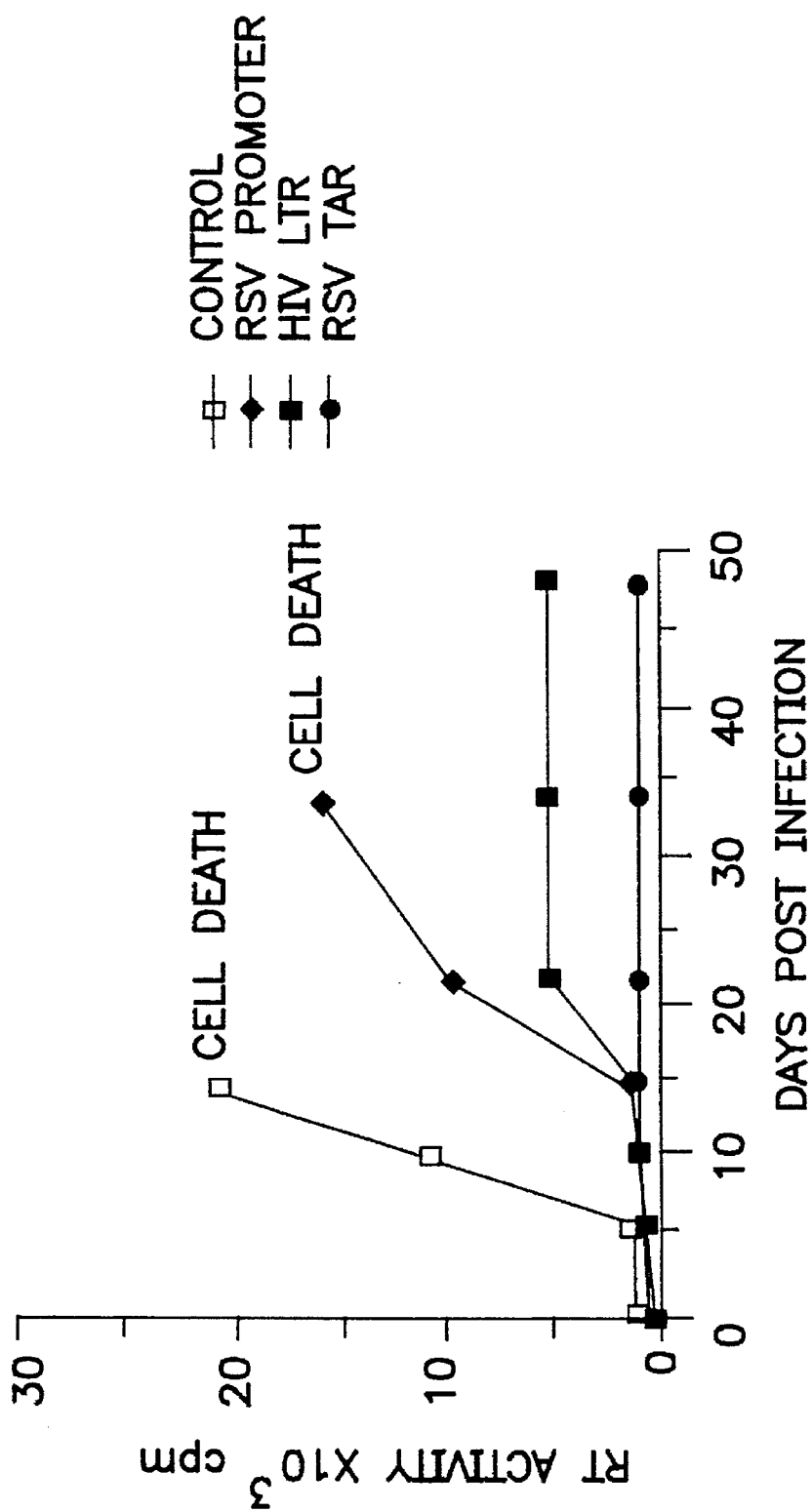
FIG. 2 depicts the level of reverse transcriptase activity in CEM cells that stably express Rev M10 from three enhancers: the RSV promoter, the HIV LTR and the RSV promoter with TAR.
Figure 3:
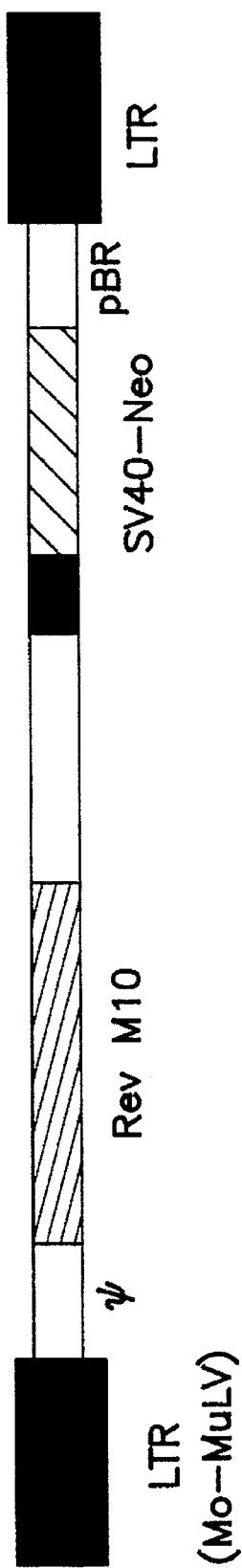
FIG. 3 depicts the structure of pLJ Rev m10 retroviral vector.

Control CEM cells and CEM cells stably expressing Rev M10 from various enhancers (RSV, HIV LTR or RSV-tar), were infected with $HIV^{Bru}$ (1:500 ratio $TCID_{50}$ HIV:CEM cells), for 2 hrs. Cells were then washed and re-suspended in fresh media. Culture supernatants were then assayed for RT activity at various times post infection. Cultures were split every 3 to 5 days dependent on growth rate. (See FIG. 2.) The plasmid for use in the particle-mediated gene transfer protocol is RSV-tar, whose structure and sequence is set forth in FIG. 7 (SEQ ID NO: 3).

Control CEM cells and CEM cells stably expressing Rev M10 (RSV/Tar construct) were infected with $HIV^{Bru}$. Cells were then washed and monitored for cytopathic effects. Control cells showed syncytia formation 5 days post infection. Rev M10 expressing cells showed no CPE for more than 50 days of cell culture. Results not shown.

Although the invention has been described with reference to the presently-preferred embodiment, it should be understood that various modifications can be made without departing from the spirit of the invention. Accordingly, the invention is limited only by the following claims.

The following articles referred to herein are incorporated by reference.

1. G. Nabel, D. Baltimore, *Nature* 326, 711 (1987).
2. K. O. Smith, K. S. Galloway, W. L. Kennell, K. K. Ogilvie, B. K. Radatus, *Antimicrob. Agents Chemother.* 22, 55 (1982).
3. A. K. Field, M. E. Davies, C. DeWitt, H. C. Perry, R. Liou, et al., *Proc. Natl. Acad. Sci. USA* 80, 4139 (1983).
4. D. F. Smee, J. C. Martin, J. P. Verheyden, T. R. Matthews, *Antimicrob. Agents Chemother.* 23, 676 (1983.)
5. H. Weintraub, J. G. Izant, R. M. Harland, *Trends Genet.* 2, 22 (1985).
6. P. J. Green, O. Pines, M. Inouye, *Ann. Rev. Biochem.* 55, 569 (1986).
7. A. R. van der Krol, J. N. M. Mol, A. R. Stuitjie, *BioTech.* 6, 958 (1988).
8. J. Hasseloff, W. L. Gerlach, *Nature* 334, 585 (1988).
9. M. Cotton, M. L. Birnstiel, *EMBO J.* 8, 3861 (1989).
10. N. Sarver, E. M. Cantin, P. S. Chang, J. A. Zaia, P. A. Ladne, et al. *Science* 247, 1222 (1990).
11. B. A. Sullenger, T. C. Lee, C. A. Smith, G. E. Ungers, E. Gilboa, *Mol. Cell. Biol.* 10, 6512 (1990).
12. B. A. Sullenger, H. F. Gallardo, G. E. Ungers, E. Gilboa, *Cell* 63, 601 (1990).
13. I. Herskowitz, *Nature* 329, 219 (1987).
14. A. D. Friedman, S. J. Triezenberg, S. L. McKnight, *Nature* 335, 452 (1988).
15. M. H. Malim, S. Bohnlein, J. Hauber, B. R. Cullen, *Cell* 58, 205 (1989).
16. M. H. Malim, W. W. Freimuth, J. Liu, T. J. Boyle, H. K. Lylerly, et al., *J. Exp. Med.* 176, 1197 (1992).
17. K. Cornetta, R. A. Morgan, A. Gillio, S. Sturm, L. Baltrucki, et al., *Hum. Gene Ther.* 2, 215 (1991).
18. K. Cornetta, R. A. Morgan, W. F. Anderson, *Hum. Gene Ther.* 2, 5 (1991).
19. K. Cornetta, R. C. Moen, K. Culver, R. A. Morgan, J. R. McLachlin, et al., *Hum. Gene Ther.* 1, 15 (1990).
20. D. Bevec, M. Dobrovnik, J. Hauber, E. Bohnlein, *Proc. Natl. Acad. Sci. USA* 89, 9870 (1992).
21. M. B. Vasudevachari, C. Battista, H. C. Lane, M. C. Psallidopoulos, B. Zhao, et al. *Virol.* 190, 269 (1992).
22. D. E. Mosier, R. J. Gulizia, S. M. Baird, D. B. Wilson, D. H. Spector, et al., *Science* 251, 791 (1991).
23. S. Kim, R. Byrn, J. Groopman, D. Baltimore, *J. Virol.* 63, 3708 (1989).
24. M. H. Malim, D. F. McCarn, L. S. Tiley, B. R. Cullen, *J. Virol.* 65, 4248 (1991).
25. R. J. Pomerantz, D. Trono, M. B. Feinberg, D. Baltimore, *Cell* 61, 1271 (1990).
26. J. Sambrook, E. F. Fritch, T. Maniatis, in *A Laboratory Manual*, Cold Spring Harbor Laboratory, Cold Spring Harbor, N.Y., (1989).
27. R. K. Saiki, D. H. Gelfand, S. Stoffel, S. J. Scharf, R. Higuchi, et al., *Science* 239, 487 (1988).
28. A. J. Korman, J. D. Frantz, J. L. Strominger, R. C. Mulligan, *Proc. Natl. Acad. Sci. USA* 84, 2150 (1987).
29. O. Danos, R. C. Mulligan, *Proc. Natl. Acad. Sci. USA* 85, 6460 (1988).
30. E. Gilboa and B. Sullenger, International Application No. PCT/US90/02656 (WO 90/13641 15 Nov. 1990).
31. L. A. Culp, W. Lin, *Biotechniques* 11, 344–351 (1991).
32. Gorman et al., *Molec. and Cell Biol.* 2, 1044 (1982).
33. M. Krieger, *Gene Transfer and Expression: A Laboratory Manual*, W. H. Freeman and Company, New York, N.Y., (1990).
34. *Methods in Enzymology*, 185, articles 38–44 (D. V. Goeddel, ed.) (1990).

We claim:

1. A recombinant nucleic acid molecule, comprising an expression control sequence and a TAR sequence, operatively linked to a negative transdominant mutant gene, wherein the negative transdominant mutant gene is a mutant of rev.

2. The recombinant nucleic acid molecule of claim 1 wherein the negative transdominant mutant gene is Rev M10.

3. The recombinant nucleic acid molecule of claim 2 wherein the negative transdominant mutant gene is the Rev M10 gene of nucleotides 700–1129 of FIG. 7 (SEQ ID NO:3).

4. A recombinant nucleic acid molecule, comprising an expression control sequence and a TAR sequence, operatively linked to a negative transdominant mutant gene, wherein the expression control sequence comprises the RSV enhancer and wherein the negative transdominant mutant gene encodes the Rev M10 transdominant mutant.

5. The recombinant nucleic acid molecule of claim 4 wherein the expression control sequence is nucleotides 37–610, nucleotides 611–699 and nucleotides 700–1129 of FIG. 7 (SEQ ID NO: 3).

6. The recombinant nucleic acid molecule of claim 4 comprising nucleotides 37–1129 of FIG. 7 (SEQ ID NO: 3).

7. The RSV tar 10 expression plasmid of FIG. 7 (SEQ ID NO: 3).

8. A retroviral vector, comprising an RNA molecule encoded by a nucleic acid molecule comprising nucleotides 37–1129 of FIG. 7 (SEQ ID NO: 3).

9. A method of inhibiting HIV expression in a T cell infected with or susceptible to HIV infection, comprising transfecting the cell with a recombinant nucleic acid molecule comprising an RSV tar Rev M10 expression vector having the sequence shown in FIG. 7 (SEQ ID NO: 3).

10. The method of claim 9 wherein the cell is a T cell and the recombinant nucleic acid molecule comprises nucleotides 37–1129 of FIG. 7 (SEQ ID NO: 3).

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 5109 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:1:

```
AATGAAAGAC  CCCACCTGTA  GGTTTGGCAA  GCTAGCTTAA  GTAACGCCAT  TTTGCAAGGC      60
ATGGAAAAAT  ACATAACTGA  GAATAGAGAA  GTTCAGATCA  AGGTCAGGAA  CAGATGGAAC     120
AGCTGAATAT  GGGCCAAACA  GGATATCTGT  GGTAAGCAGT  TCCTGCCCCG  GCTCAGGGCC     180
AAGAACAGAT  GGAACAGCTG  AATATGGGCC  AAACAGGATA  TCTGTGGTAA  GCAGTTCCTG     240
CCCCGGCTCA  GGGCCAAGAA  CAGATGGTCC  CCAGATGCGG  TCCAGCCCTC  AGCAGTTTCT     300
AGAGAACCAT  CAGATGTTTC  AGGGTGCCC   CAAGGACCTG  AAATGACCCT  GTGCCTTATT     360
TGAACTAACC  AATCAGTTCG  CTTCTCGCTT  CTGTTCGCGC  GCTTCTGCTC  CCCGAGCTCA     420
ATAAAGAGC   CCACAACCCC  TCACTCGGGG  CGCCAGTCCT  CCGATTGACT  GAGTCGCCCG     480
GGTACCCGTG  TATCCAATAA  ACCCTCTTGC  AGTTGCATCC  GACTTGTGGT  CTCGCTGTTC     540
CTTGGGAGGG  TCTCCTCTGA  GTGATTGACT  ACCCGTCAGC  GGGGGTCTTT  CATTTGGGGG     600
CTCGTCCGGG  ATCGGGAGAC  CCCTGCCCAG  GGACCACCGA  CCCACCACCG  GGAGGTAAGC     660
TGGCCAGCAA  CTTATCTGTG  TCTGTCCGAT  TGTCTAGTGT  CTATGACTGA  TTTTATGCGC     720
CTGCGTCGGT  ACTAGTTAGC  TAACTAGCTC  TGTATCTGGC  GGACCCGTGG  TGGAACTGAC     780
GAGTTCGGAA  CACCCGGCCG  CAACCCTGGG  AGACGTCCCA  GGGACTTCGG  GGGCCGTTTT     840
TGTGGCCCGA  CCTGAGTCCA  AAAATCCCGA  TCGTTTTGGA  CTCTTTGGTG  CACCCCCCTT     900
AGAGGAGGGA  TATGTGGTTC  TGGTAGGAGA  CGAGAACCTA  AAACAGTTCC  CGCCTCCGTC     960
TGAATTTTTG  CTTTCGGTTT  GGGACCGAAG  CCGCGCCGCG  CGTCTTGTCT  GCTGCAGCAT    1020
CGTTCTGTGT  TGGATCCCAT  GGCAGGAAGA  AGCGGAGACA  GCGACGAAGA  CCTCCTCAAG    1080
GCAGTCAGAC  TCATCAAGTT  TCTCTATCAA  AGCAACCCAC  CTCCCAATCC  CGAGGGGACC    1140
CGACAGGCCC  GAAGGAATAG  AAGAAGAAGG  TGGAGAGAGA  GACAGAGACA  GATCCATTCG    1200
ATTAGTGAAC  GGATCCTTAG  CACTTATCTG  GGACGATCTG  CGAGCCTGTG  CCTCTTCAGC    1260
TACCACCAGA  TCTGAGACTT  ACTCTTGATT  GTAACGAGGA  TTGTGGAACT  TCTGGGACGC    1320
AGGGGGTGGG  AAGCCCTCAA  ATATTGGTGG  AATCTCCTAC  AGTATTGGAG  TCAGGAACTA    1380
AAGAATAGTG  CTGTTAGCTT  GCTCAATGCC  ACAGCTATAG  CAGTAGCTGA  GGGGACAGAT    1440
AGGGTTATAG  AAGTAGTACA  AGAAGCTTGT  AGAGCTATTC  GCCACATACC  TAGAAGAATA    1500
AGACAGGGCT  TGGAAAGGAT  TTGCTATAA   GATGGGTGGC  AAGTGGTCAA  AAAGTAGTGT    1560
GATTGGATGG  CTTACTGTAA  GGGAAAGAAT  GAGACGAGCT  GAGCCAGCAG  CAGATGGGGT    1620
GGGAGCAGCA  TCTCGAGCAG  CTGTGGAATG  TGTGTCAGTT  AGGGTGTGGA  AAGTCCCCAG    1680
GCTCCCCAGC  AGGCAGAAGT  ATGCAAAGCA  TGCATCTCAA  TTAGTCAGCA  ACCAGGTGTG    1740
CAAAGTCCCC  AGGCTCCCCA  GCAGGCAGAA  GTATGCAAAG  CATGCATCTC  AATTAGTCAG    1800
CAACCATAGT  CCCGCCCCTA  ACTCCGCCCA  TCCCGCCCCT  AACTCCGCCC  AGTTCCGCCC    1860
```

```
ATTCTCCGCC CCATGGCTGA CTAATTTTTT TTATTTATGC AGAGGCCGAG GCCGCCTCGG    1920
CCTCTGAGCT ATTCCAGAAG TAGTGAGGAG GCTTTTTTGG AGGCCTAGGC TTTTGCAAAA    1980
AGCTTCACGC TGCCGCAAGC ACTCAGGGCG CAAGGGCTGC TAAAGGAAGC GGAACACGTA    2040
GAAAGCCAGT CCGCAGAAAC GGTGCTGACC CCGGATGAAT GTCAGCTACT GGGCTATCTG    2100
GACAAGGGAA AACGCAAGCG CAAAGAGAAA GCAGGTAGCT TGCAGTGGGC TTACATGGCG    2160
ATAGCTAGAC TGGGCGGTTT TATGGACAGC AAGCGAACCG GAATTGCCAG CTGGGGCGCC    2220
CTCTGGTAGC CCTGCAAAGC CCTGCAAAGT AAACTGGATG GCTTTCTTGC CGCCAAGGAT    2280
CTGATGGCGC AGGGGATCAA GATCTGATCA AGAGACAGGA TGAGGATCGT TTCGCATGAT    2340
TGAACAAGAT GGATTGCACG CAGGTTCTCC GGCCGCTTGG GTGGAGAGGC TATTCGGCTA    2400
TGACTGGGCA CAACAGACAA TCGGCTGCTC TGATGCCGCC GTGTTCCGGC TGTCAGCGCA    2460
GGGGCGCCCG GTTCTTTTTG TCAAGACCGA CCTGTCCGGT GCCCTGAATG AACTGCAGGA    2520
CGAGGCAGCG CGGCTATCGT GGCTGGCCAC GACGGGCGTT CCTTGCGCAG CTGTGCTCGA    2580
CGTTGTCACT GAAGCGGGAA GGGACTGGCT GCTATTGGGC GAAGTGCCGG GGCAGGATCT    2640
CCTGTCATCT CACCTTGCTC CTGCCGAGAA AGTATCCATC ATGGCTGATG CAATGCGGCG    2700
GCTGCATACG CTTGATCCGG CTACCTGCCC ATTCGACCAC CAAGCGAAAC ATCGCATCGA    2760
GCGAGC Y CGT ACTCGGATGG AAGCCGGTCT TGTCGATCAG GATGATCTGG ACGAAGAGCA    2820
TCAGGGGCTC GCGCCAGCCG AACTGTTCGC CAGGCTCAAG GCGCGCATGC CCGACGGCGA    2880
GGATCTCGTC GTGACCCATG GCGATGCCTG CTTGCCGAAT ATCATGGTGG AAAATGGCCG    2940
CTTTTCTGGA TTCATCGACT GTGGCCGGCT GGGTGTGGCG GACCGCTATC AGGACATAGC    3000
GTTGGCTACC CGTGATATTG CTGAAGAGCT TGGCGGCGAA TGGGCTGACC GCTTCCTCGT    3060
GCTTTACGGT ATCGCCGCTC CCGATTCGCA GCGCATCGCC TTCTATCGCC TTCTTGAGGA    3120
GTTCTTCTGA GCGGGACTCT GGGGTTCGAA ATGACCGACC AAGCGACGCC CAACCTGCCA    3180
TCACGAGATT TCGATTCCAC CGCCGCCTTC TATGAAAGGT TGGGCTTCGG AATCGTTTTC    3240
CGGGACGCCG GCTGGATGAT CCTCCAGCGC GGGGATCTCA TGCTGGAGTT CTTCGCCCAC    3300
CCCCGCGTTG CTGGCGTTTT CCATAGGCT CCGCCCCCT GACGAGCATC ACAAAAATCG    3360
ACGCTCAAGT CAGAGGTGGC GAAACCCGAC AGGACTATAA AGATACCAGG CGTTTCCCCC    3420
TGGAAGCTCC CTCGTGCGCT CTCCTGTTCC GACCCTGCCG CTTACCGGAT ACCTGTCCGC    3480
CTTTCTCCCT TCGGGAAGCG TGGCGCTTTC TCATAGCTCA CGCTGTAGGT ATCTCAGTTC    3540
GGTGTAGGTC GTTCGCTCCA AGCTGGGCTG TGTGCACGAA CCCCCCGTTC AGCCCGACCG    3600
CTGCGCCTTA TCCGGTAACT ATCGTCTTGA GTCCAACCCG GTAAGACACG ACTTATCGCC    3660
ACTGGCAGCA GCCACTGGTA ACAGGATTAG CAGAGCGAGG TATGTAGGCG GTGCTACAGA    3720
GTTCTTGAAG TGGTGGCCTA ACTACGGCTA CACTAGAAGG ACAGTATTTG GTATCTGCGC    3780
TCTGCTGAAG CCAGTTACCT TCGGAAAAAG AGTTGGTAGC TCTTGATCCG GCAAACAAAC    3840
CACCGCTGGT AGCGGTGGTT TTTTGTTTG CAAGCAGCAG ATTACGTCGG TGTCGTTAAC    3900
CCTGGCCCTA TTATTGGGTG GACTAACCAT GGGGGGAATT GCCGCTGGAA TAGGAACAGG    3960
GACTACTGCT CTAATGGCCA CTCAGCAATT CCAGCAGCTC AAGCCGCAG TACAGGATGA    4020
TCTCAGGGAG GTTGAAAAAT CAATCTCTAA CCTAGAAAAG TCTCTCACTT CCCTGTCTGA    4080
AGTTGTCCTA CAGAATCGAA GGGGCCTAGA CTTGTTATTT CTAAAGAAG GAGGGCTGTG    4140
TGCTGCTCTA AAAGAAGAAT GTTGCTTCTA TGCGGACCAC ACAGGACTAG TGAGAGACAG    4200
CATGGCCAAA TTGAGAGAGA GGCTTAATCA GAGACAGAAA CTGTTTGAGT CAACTCAAGG    4260
```

-continued

| | | | | | | |
|---|---|---|---|---|---|---|
| ATGGTTTGAG | GGACTGTTTA | ACAGATCCCC | TTGGTTTACC | ACCTTGATAT | CTACCATTAT | 4320 |
| GGGACCCCTC | ATTGTACTCC | TAATGATTTT | GCTCTTCGGA | CCCTGCATTC | TTAATCGATT | 4380 |
| AGTCCAATTT | GTTAAAGACA | GGATATCAGT | GGTCCAGGCT | CTAGTTTTGA | CTCAACAATA | 4440 |
| TCACCAGCTG | AAGCCTATAG | AGTACGAGCC | ATAGATAAAA | TAAAAGATTT | TATTTAGTCT | 4500 |
| CCAGAAAAAG | GGGGGAATGA | AAGACCCCAC | CTGTAGGTTT | GGCAAGCTAG | CTTAAGTAAC | 4560 |
| GCCATTTTGC | AAGGCATGGA | AAAATACATA | ACTGAGAATA | GAGAAGTTCA | GATCAAGGTC | 4620 |
| AGGAACAGAT | GGAACAGCTG | AATATGGGCC | AAACAGGATA | TCTGTGGTAA | GCAGTTCCTG | 4680 |
| CCCCGGCTCA | GGGCCAAGAA | CAGATGGAAC | AGCTGAATAT | GGGCCAAACA | GGATATCTGT | 4740 |
| GGTAAGCAGT | TCCTGCCCCG | GCTCAGGGCC | AAGAACAGAT | GGTCCCAGA | TGCGGTCCAG | 4800 |
| CCCTCAGCAG | TTTCTAGAGA | ACCATCAGAT | GTTCCAGGG | TGCCCCAAGG | ACCTGAAATG | 4860 |
| ACCCTGTGCC | TTATTTGAAC | TAACCAATCA | GTTCGCTTCT | CGCTTCTGTT | CGCGCGCTTC | 4920 |
| TGCTCCCCGA | GCTCAATAAA | AGAGCCCACA | ACCCCTCACT | CGGGGCGCCA | GTCCTCCGAT | 4980 |
| TGACTGAGTC | GCCCGGGTAC | CCGTGTATCC | AATAAACCCT | CTTGCAGTTG | CATCCGACTT | 5040 |
| GTGGTCTCGC | TGTTCCTTGG | GAGGGTCTCC | TCTGAGTGAT | TGACTACCCG | TCAGCGGGGG | 5100 |
| TCTTTCATT | | | | | | 5109 |

( 2 ) INFORMATION FOR SEQ ID NO:2:

( i ) SEQUENCE CHARACTERISTICS:
        ( A ) LENGTH: 5176 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:2:

| | | | | | | |
|---|---|---|---|---|---|---|
| AATGAAAGAC | CCCACCTGTA | GGTTTGGCAA | GCTAGCTTAA | GTAACGCCAT | TTGCAAGGC | 60 |
| ATGGAAAAAT | ACATAACTGA | GAATAGAGAA | GTTCAGATCA | AGGTCAGGAA | CAGATGGAAC | 120 |
| AGCTGAATAT | GGGCCAAACA | GGATATCTGT | GGTAAGCAGT | TCCTGCCCCG | GCTCAGGGCC | 180 |
| AAGAACAGAT | GGAACAGCTG | AATATGGGCC | AAACAGGATA | TCTGTGGTAA | GCAGTTCCTG | 240 |
| CCCCGGCTCA | GGGCCAAGAA | CAGATGGTCC | CCAGATGCGG | TCCAGCCCTC | AGCAGTTTCT | 300 |
| AGAGAACCAT | CAGATGTTTC | CAGGGTGCCC | CAAGGACCTG | AAATGACCCT | GTGCCTTATT | 360 |
| TGAACTAACC | AATCAGTTCG | CTTCTCGCTT | CTGTTCGCGC | GCTTCTGCTC | CCCGAGCTCA | 420 |
| ATAAAGAGC | CCACAACCCC | TCACTCGGGG | CGCCAGTCCT | CCGATTGACT | GAGTCGCCCG | 480 |
| GGTACCCGTG | TATCCAATAA | ACCCTCTTGC | AGTTGCATCC | GACTTGTGGT | CTCGCTGTTC | 540 |
| CTTGGGAGGG | TCTCCTCTGA | GTGATTGACT | ACCCGTCAGC | GGGGGTCTTT | CATTTGGGGG | 600 |
| CTCGTCCGGG | ATCGGGAGAC | CCCTGCCCAG | GGACCACCGA | CCCACCACCG | GGAGGTAAGC | 660 |
| TGGCCAGCAA | CTTATCTGTG | TCTGTCCGAT | TGTCTAGTGT | CTATGACTGA | TTTTATGCGC | 720 |
| CTGCGTCGGT | ACTAGTTAGC | TAACTAGCTC | TGTATCTGGC | GGACCCGTGG | TGGAACTGAC | 780 |
| GAGTTCGGAA | CACCCGGCCG | CAACCCTGGG | AGACGTCCA | GGGACTTCGG | GGGCCGTTTT | 840 |
| TGTGGCCCGA | CCTGAGTCCA | AAAATCCCGA | TCGTTTTGGA | CTCTTTGGTG | CACCCCCCTT | 900 |
| AGAGGAGGGA | TATGTGGTTC | TGGTAGGAGA | CGAGAACCTA | AACAGTTCC | CGCCTCCGTC | 960 |
| TGAATTTTTG | CTTTCGGTTT | GGGACCGAAG | CCGCGCCGCG | CGTCTTGTCT | GCTGCAGCAT | 1020 |
| CGTTCTGTGT | TGGGATCAGC | TCGTTTAGTA | AGTCAAGCTT | AAGTGACCAG | CTACAGTCGG | 1080 |
| AAACCATCAG | CAAGAGGTCA | TTGTTCACGC | AGGAAGAAGC | GGAGACAGCG | ACGAAGACCT | 1140 |
| CCTCAAGGCA | GTCAGACTCA | TCAAGTTTCT | CTATCAAAGC | AACCCACCTC | CCAATCCCGA | 1200 |

```
GGGGACCCGA  CAGGCCCGAA  GGAATAGAAG  AAGAAGGTGG  AGAGAGAGAC  AGAGACAGAT   1260
CCATTCGATT  AGTGAACGGA  TCCTTAGCAC  TTATCTGGGA  CGATCTGCGA  GCCTGTGCCT   1320
CTTCAGCTAC  CACCAGATCT  GAGACTTACT  CTTGATTGTA  ACGAGGATTG  TGGAACTTCT   1380
GGGACGCAGG  GGGTGGGAAG  CCCTCAAATA  TTGGTGGAAT  CTCCTACAGT  ATTGGAGTCA   1440
GGAACTAAAG  AATAGTGCTG  TTAGCTTGCT  CAATGCCACA  GCTATAGCAG  TAGCTGAGGG   1500
GACAGATAGG  GTTATAGAAG  TAGTACAAGA  AGCTTGTAGA  GCTATTCGCC  ACATACCTAG   1560
AAGAATAAGA  CAGGGCTTGG  AAAGGATTTT  GCTATAAGAT  GGGTGGCAAG  TGGTCAAAAA   1620
GTAGTGTGAT  TGGATGGCTT  ACTGTAAGGG  AAAGAATGAG  ACGAGCTGAG  CCAGCAGCAG   1680
ATGGGGTGGG  AGCAGCATCT  CGAGCAGCTG  TGGAATGTGT  GTCAGTTAGG  GTGTGGAAAG   1740
TCCCCAGGCT  CCCCAGCAGG  CAGAAGTATG  CAAAGCATGC  ATCTCAATTA  GTCAGCAACC   1800
AGGTGTGGAA  AGTCCCCAGG  CTCCCCAGCA  GGCAGAAGTA  TGCAAAGCAT  GCATCTCAAT   1860
TAGTCAGCAA  CCATAGTCCC  GCCCCTAACT  CCGCCCATCC  CGCCCCTAAC  TCCGCCCAGT   1920
TCCGCCCATT  CTCCGCCCCA  TGGCTGACTA  ATTTTTTTA   TTTATGCAGA  GGCCGAGGCC   1980
GCCTCGGCCT  CTGAGCTATT  CCAGAAGTAG  TGAGGAGGCT  TTTTGGAGG   CCTAGGCTTT   2040
TGCAAAAGC   TTCACGCTGC  CGCAAGCACT  CAGGGCGCAA  GGGCTGCTAA  GGAAGCGGA    2100
ACACGTAGAA  AGCCAGTCCG  CAGAAACGGT  GCTGACCCCG  GATGAATGTC  AGCTACTGGG   2160
CTATCTGGAC  AAGGGAAAAC  GCAAGCGCAA  AGAGAAAGCA  GGTAGCTTGC  AGTGGGCTTA   2220
CATGGCGATA  GCTAGACTGG  GCGGTTTTAT  GGACAGCAAG  CGAACCGGAA  TTGCCAGCTG   2280
GGGCGCCCTC  TGGTAGCCCT  GCAAAGCCCT  GCAAAGTAAA  CTGGATGGCT  TTCTTGCCGC   2340
CAAGGATCTG  ATGGCGCAGG  GGATCAAGAT  CTGATCAAGA  GACAGGATGA  GGATCGTTTC   2400
GCATGATTGA  ACAAGATGGA  TTGCACGCAG  GTTCTCCGGC  CGCTTGGGTG  GAGAGGCTAT   2460
TCGGCTATGA  CTGGGCACAA  CAGACAATCG  GCTGCTCTGA  TGCCGCCGTG  TTCCGGCTGT   2520
CAGCGCAGGG  GCGCCCGGTT  CTTTTTGTCA  AGACCGACCT  GTCCGGTGCC  CTGAATGAAC   2580
TGCAGGACGA  GGCAGCGCGG  CTATCGTGGC  TGGCCACGAC  GGGCGTTCCT  TGCGCAGCTG   2640
TGCTCGACGT  TGTCACTGAA  GCGGGAAGGG  ACTGGCTGCT  ATTGGGCGAA  GTGCCGGGGC   2700
AGGATCTCCT  GTCATCTCAC  CTTGCTCCTG  CCGAGAAAGT  ATCCATCATG  GCTGATGCAA   2760
TGCGGCGGCT  GCATACGCTT  GATCCGGCTA  CCTGCCCATT  CGACCACCAA  GCGAAACATC   2820
GCATCGAGCG  AGC Y CGTACT  CGGATGGAAG  CCGGTCTTGT  CGATCAGGAT  GATCTGGACG   2880
AAGAGCATCA  GGGGCTCGCG  CCAGCCGAAC  TGTTCGCCAG  GCTCAAGGCG  CGCATGCCCG   2940
ACGGCGAGGA  TCTCGTCGTG  ACCCATGGCG  ATGCCTGCTT  GCCGAATATC  ATGGTGGAAA   3000
ATGGCCGCTT  TTCTGGATTC  ATCGACTGTG  GCCGGCTGGG  TGTGGCGGAC  CGCTATCAGG   3060
ACATAGCGTT  GGCTACCCGT  GATATTGCTG  AAGAGCTTGG  CGGCGAATGG  GCTGACCGCT   3120
TCCTCGTGCT  TTACGGTATC  GCCGCTCCCG  ATTCGCAGCG  CATCGCCTTC  TATCGCCTTC   3180
TTGAGGAGTT  CTTCTGAGCG  GGACTCTGGG  GTTCGAAATG  ACCGACCAAG  CGACGCCCAA   3240
CCTGCCATCA  CGAGATTTCG  ATTCCACCGC  CGCCTTCTAT  GAAAGGTTGG  GCTTCGGAAT   3300
CGTTTTCCGG  GACGCCGGCT  GGATGATCCT  CCAGCGCGGG  GATCTCATGC  TGGAGTTCTT   3360
CGCCCACCCC  CGCGTTGCTG  GCGTTTTCC   ATAGGCTCCG  CCCCCTGAC   GAGCATCACA   3420
AAAATCGACG  CTCAAGTCAG  AGGTGGCGAA  ACCCGACAGG  ACTATAAAGA  TACCAGGCGT   3480
TTCCCCCTGG  AAGCTCCCTC  GTGCGCTCTC  CTGTTCCGAC  CCTGCCGCTT  ACCGGATACC   3540
TGTCCGCCTT  TCTCCCTTCG  GGAAGCGTGG  CGCTTTCTCA  TAGCTCACGC  TGTAGGTATC   3600
```

-continued

```
TCAGTTCGGT GTAGGTCGTT CGCTCCAAGC TGGGCTGTGT GCACGAACCC CCCGTTCAGC   3660
CCGACCGCTG CGCCTTATCC GGTAACTATC GTCTTGAGTC CAACCCGGTA AGACACGACT   3720
TATCGCCACT GGCAGCAGCC ACTGGTAACA GGATTAGCAG AGCGAGGTAT GTAGGCGGTG   3780
CTACAGAGTT CTTGAAGTGG TGGCCTAACT ACGGCTACAC TAGAAGGACA GTATTTGGTA   3840
TCTGCGCTCT GCTGAAGCCA GTTACCTTCG GAAAAAGAGT TGGTAGCTCT TGATCCGGCA   3900
AACAAACCAC CGCTGGTAGC GGTGGTTTTT TTGTTTGCAA GCAGCAGATT ACGTCGGTGT   3960
CGTTAACCCT GGCCCTATTA TTGGGTGGAC TAACCATGGG GGGAATTGCC GCTGGAATAG   4020
GAACAGGGAC TACTGCTCTA ATGGCCACTC AGCAATTCCA GCAGCTCCAA GCCGCAGTAC   4080
AGGATGATCT CAGGGAGGTT GAAAAATCAA TCTCTAACCT AGAAAGTCT CTCACTTCCC    4140
TGTCTGAAGT TGTCCTACAG AATCGAAGGG GCCTAGACTT GTTATTTCTA AAGAAGGAG    4200
GGCTGTGTGC TGCTCTAAAA GAAGAATGTT GCTTCTATGC GGACCACACA GGACTAGTGA   4260
GAGACAGCAT GGCCAAATTG AGAGAGAGGC TTAATCAGAG ACAGAAACTG TTTGAGTCAA   4320
CTCAAGGATG GTTTGAGGGA CTGTTTAACA GATCCCCTTG GTTACCACC TTGATATCTA    4380
CCATTATGGG ACCCCTCATT GTACTCCTAA TGATTTTGCT CTTCGGACCC TGCATTCTTA   4440
ATCGATTAGT CCAATTTGTT AAAGACAGGA TATCAGTGGT CCAGGCTCTA GTTTGACTC    4500
AACAATATCA CCAGCTGAAG CCTATAGAGT ACGAGCCATA GATAAAATAA AGATTTTAT    4560
TTAGTCTCCA GAAAAAGGGG GGAATGAAAG ACCCCACCTG TAGGTTTGGC AAGCTAGCTT   4620
AAGTAACGCC ATTTTGCAAG GCATGGAAAA ATACATAACT GAGAATAGAG AAGTTCAGAT   4680
CAAGGTCAGG AACAGATGGA ACAGCTGAAT ATGGGCCAAA CAGGATATCT GTGGTAAGCA   4740
GTTCCTGCCC CGGCTCAGGG CCAAGAACAG ATGGAACAGC TGAATATGGG CCAAACAGGA   4800
TATCTGTGGT AAGCAGTTCC TGCCCCGGCT CAGGGCCAAG AACAGATGGT CCCCAGATGC   4860
GGTCCAGCCC TCAGCAGTTT CTAGAGAACC ATCAGATGTT CCAGGGTGC CCCAAGGACC    4920
TGAAATGACC CTGTGCCTTA TTTGAACTAA CCAATCAGTT CGCTTCTCGC TTCTGTTCGC   4980
GCGCTTCTGC TCCCCGAGCT CAATAAAAGA GCCCACAACC CCTCACTCGG GGCGCCAGTC   5040
CTCCGATTGA CTGAGTCGCC CGGGTACCCG TGTATCCAAT AAACCCTCTT GCAGTTGCAT   5100
CCGACTTGTG GTCTCGCTGT TCCTTGGGAG GGTCTCCTCT GAGTGATTGA CTACCCGTCA   5160
GCGGGGGTCT TTCATT                                                   5176
```

( 2 ) INFORMATION FOR SEQ ID NO:3:

( i ) SEQUENCE CHARACTERISTICS:
        ( A ) LENGTH: 5653 base pairs
        ( B ) TYPE: nucleic acid
        ( C ) STRANDEDNESS: double
        ( D ) TOPOLOGY: linear ( x i ) SEQUENCE DESCRIPTION: SEQ ID NO:3:

```
GACGGATCGG GAGATCTCCC GATCCCCTAT GGTCGACTCT CAGTACAATC TGCTCTGATG     60
CCGCATAGTT AAGCCAGTAT CTGCTCCCTG CTTGTGTGTT GGAGGTCGCT GAGTAGTGCG    120
CGAGCAAAAT TTAAGCTACA ACAAGGCAAG GCTTGACCGA CAATTGCATG AAGAATCTGC    180
TTAGGGTTAG GCGTTTTGCG CTGCTTCGCG ATGTACGGGC CAGATATACG CGTATCTGAG    240
GGGACTAGGG TGTGTTTAGG CGAAAAGCGG GGCTTCGGTT GTACGCGGTT AGGAGTCCCC    300
TCAGGATATA GTAGTTTCGC TTTTGCATAG GGAGGGGGAA ATGTAGTCTT ATGCAATACA    360
CTTGTAGTCT TGCAACATGG TAACGATGAG TTAGCAACAT GCCTTACAAG GAGAGAAAAA    420
```

```
GCACCGTGCA TGCCGATTGG TGGAAGTAAG GTGGTACGAT CGTGCCTTAT TAGGAAGGCA    480
ACAGACAGGT CTGACATGGA TTGGACGAAC CACTGAATTC CGCATTGCAG AGATAATTGT    540
ATTTAAGTGC CTAGCTCGAT ACAATAAACG CCATTTGACC ATTCACCACA TTGGTGTGCA    600
CCTCCAAGCT CTGCTTTTTG CCTGTACTGG GTCTCTCTGG TTAGACCAGA TCTGAGCCTG    660
GGAGCTCTCT GGCTAGCTAG GAACCCACT GCTTAAGCTC ATGGCAGGAA GAAGCGGAGA     720
CAGCGACGAA GACCTCCTCA AGGCAGTCAG ACTCATCAAG TTTCTCTATC AAAGCAACCC    780
ACCTCCCAAT CCCGAGGGGA CCCGACAGGC CCGAAGGAAT AGAAGAAGAA GGTGGAGAGA    840
GAGACAGAGA CAGATCCATT CGATTAGTGA ACGGATCCTT AGCACTTATC TGGGACGATC    900
TGCGAGCCTG TGCCTCTTCA GCTACCACCA GATCTGAGAC TTACTCTTGA TTGTAACGAG    960
GATTGTGGAA CTTCTGGGAC GCAGGGGGTG GGAAGCCCTC AAATATTGGT GGAATCTCCT   1020
ACAGTATTGG AGTCAGGAAC TAAAGAATAG TGCTGTTAGC TTGCTCAATG CCACAGCTAT   1080
AGCAGTAGCT GAGGGGACAG ATAGGGTTAT AGAAGTAGTA CAAGAAGCTC TAGAGCTCGC   1140
TGATCAGCCT CGACTGTGCC TTCTAGTTGC CAGCCATCTG TTGTTTGCCC CTCCCCCGTG   1200
CCTTCCTTGA CCCTGGAAGG TGCCACTCCC ACTGTCCTTT CCTAATAAAA TGAGGAAATT   1260
GCATCGCATT GTCTGAGTAG GTGTCATTCT ATTCTGGGGG GTGGGGTGGG GCAGGACAGC   1320
AAGGGGGAGG ATTGGGAAGA CAATAGCAGG CATGCTGGGG ATGCGGTGGG CTCTATGGCT   1380
TCTGAGGCGG AAAGAACCAG CTGGGGCTCG AGGGGGGATC CCCACGCGCC CTGTAGCGGC   1440
GCATTAAGCG CGGCGGGTGT GGTGGTTACG CGCAGCGTGA CCGCTACACT TGCCAGCGCC   1500
CTAGCGCCCG CTCCTTTCGC TTTCTTCCCT TCCTTTCTCG CCACGTTCGC CGGCTTTCCC   1560
CGTCAAGCTC TAAATCGGGG CATCCCTTTA GGGTTCCGAT TTAGTGCTTT ACGGCACCTC   1620
GACCCCAAAA AACTTGATTA GGGTGATGGT TCACGTAGTG GGCCATCGCC CTGATAGACG   1680
GTTTTCGCC CTTTGACGTT GGAGTCCACG TTCTTTAATA GTGGACTCTT GTTCCAAACT   1740
GGAACAACAC TCAACCCTAT CTCGGTCTAT TCTTTTGATT TATAAGGGAT TTTGGGGATT   1800
TCGGCCTATT GGTTAAAAAA TGAGCTGATT TAACAAAAAT TTAACGCGAA TTTTAACAAA   1860
ATATTAACGT TTACAATTTA AATATTTGCT TATACAATCT TCCTGTTTTT GGGGCTTTTC   1920
TGATTATCAA CCGGGGTGGG TACCGAGCTC GAATTCTGTG GAATGTGTGT CAGTTAGGGT   1980
GTGGAAAGTC CCCAGGCTCC CCAGGCAGGC AGAAGTATGC AAAGCATGCA TCTCAATTAG   2040
TCAGCAACCA GGTGTGGAAA GTCCCCAGGC TCCCCAGCAG GCAGAAGTAT GCAAAGCATG   2100
CATCTCAATT AGTCAGCAAC CATAGTCCCG CCCCTAACTC CGCCCATCCC GCCCCTAACT   2160
CCGCCCAGTT CCGCCCATTC TCCGCCCCAT GGCTGACTAA TTTTTTTTAT TTATGCAGAG   2220
GCCGAGGCCG CCTCGGCCTC TGAGCTATTC CAGAAGTAGT GAGGAGGCTT TTTTGGAGGC   2280
CTAGGCTTTT GCAAAAAGCT CCCGGGAGCT TGGATATCCA TTTTCGGATC TGATCAAGAG   2340
ACAGGATGAG GATCGTTTCG CATGATTGAA CAAGATGGAT TGCACGCAGG TTCTCCGGCC   2400
GCTTGGGTGG AGAGGCTATT CGGCTATGAC TGGGCACAAC AGACAATCGG CTGCTCTGAT   2460
GCCGCCGTGT TCCGGCTGTC AGCGCAGGGG CGCCCGGTTC TTTTTGTCAA GACCGACCTG   2520
TCCGGTGCCC TGAATGAACT GCAGGACGAG GCAGCGCGGC TATCGTGGCT GGCCACGACG   2580
GGCGTTCCTT GCGCAGCTGT GCTCGACGTT GTCACTGAAG CGGGAAGGGA CTGGCTGCTA   2640
TTGGGCGAAG TGCCGGGGCA GGATCTCCTG TCATCTCACC TTGCTCCTGC CGAGAAAGTA   2700
TCCATCATGG CTGATGCAAT GCGGCGGCTG CATACGCTTG ATCCGGCTAC CTGCCCATTC   2760
GACCACCAAG CGAAACATCG CATCGAGCGA GCACGTACTC GGATGGAAGC CGGTCTTGTC   2820
```

```
GATCAGGATG ATCTGGACGA AGAGCATCAG GGGCTCGCGC CAGCCGAACT GTTCGCCAGG    2880
CTCAAGGCGC GCATGCCCGA CGGCGAGGAT CTCGTCGTGA CCCATGGCGA TGCCTGCTTG    2940
CCGAATATCA TGGTGGAAAA TGGCCGCTTT TCTGGATTCA TCGACTGTGG CCGGCTGGGT    3000
GTGGCGGACC GCTATCAGGA CATAGCGTTG GCTACCCGTG ATATTGCTGA AGAGCTTGGC    3060
GGCGAATGGG CTGACCGCTT CCTCGTGCTT TACGGTATCG CCGCTCCCGA TTCGCAGCGC    3120
ATCGCCTTCT ATCGCCTTCT TGACGAGTTC TTCTGAGCGG GACTCTGGGG TTCGAAATGA    3180
CCGACCAAGC GACGCCCAAC CTGCCATCAC GAGATTTCGA TTCCACCGCC GCCTTCTATG    3240
AAAGGTTGGG CTTCGGAATC GTTTTCCGGG ACGCCGGCTG GATGATCCTC CAGCGCGGGG    3300
ATCTCATGCT GGAGTTCTTC GCCCACCCCA ACTTGTTTAT TGCAGCTTAT AATGGTTACA    3360
AATAAAGCAA TAGCATCACA AATTTCACAA ATAAAGCATT TTTTCACTG CATTCTAGTT     3420
GTGGTTTGTC CAAACTCATC AATGTATCTT ATCATGTCTG GATCCCGTCG ACCTCGAGAG    3480
CTTGGCGTAA TCATGGTCAT AGCTGTTTCC TGTGTGAAAT TGTTATCCGC TCACAATTCC    3540
ACACAACATA CGAGCCGGAA GCATAAAGTG TAAAGCCTGG GGTGCCTAAT GAGTGAGCTA    3600
ACTCACATTA ATTGCGTTGC GCTCACTGCC CGCTTTCCAG TCGGGAAACC TGTCGTGCCA    3660
GCTGCATTAA TGAATCGGCC AACGCGCGGG GAGAGGCGGT TTGCGTATTG GGCGCTCTTC    3720
CGCTTCCTCG CTCACTGACT CGCTGCGCTC GGTCGTTCGG CTGCGGCGAG CGGTATCAGC    3780
TCACTCAAAG GCGGTAATAC GGTTATCCAC AGAATCAGGG GATAACGCAG GAAAGAACAT    3840
GTGAGCAAAA GGCCAGCAAA AGGCCAGGAA CCGTAAAAAG GCCGCGTTGC TGGCGTTTTT    3900
CCATAGGCTC CGCCCCCCTG ACGAGCATCA CAAAAATCGA CGCTCAAGTC AGAGGTGGCG    3960
AAACCCGACA GGACTATAAA GATACCAGGC GTTTCCCCCT GGAAGCTCCC TCGTGCGCTC    4020
TCCTGTTCCG ACCCTGCCGC TTACCGGATA CCTGTCCGCC TTTCTCCCTT CGGGAAGCGT    4080
GGCGCTTTCT CAATGCTCAC GCTGTAGGTA TCTCAGTTCG GTGTAGGTCG TTCGCTCCAA    4140
GCTGGGCTGT GTGCACGAAC CCCCCGTTCA GCCCGACCGC TGCGCCTTAT CCGGTAACTA    4200
TCGTCTTGAG TCCAACCCGG TAAGACACGA CTTATCGCCA CTGGCAGCAG CCACTGGTAA    4260
CAGGATTAGC AGAGCGAGGT ATGTAGGCGG TGCTACAGAG TTCTTGAAGT GGTGGCCTAA    4320
CTACGGCTAC ACTAGAAGGA CAGTATTTGG TATCTGCGCT CTGCTGAAGC CAGTTACCTT    4380
CGGAAAAAGA GTTGGTAGCT CTTGATCCGG CAAACAAACC ACCGCTGGTA GCGGTGGTTT    4440
TTTTGTTTGC AAGCAGCAGA TTACGCGCAG AAAAAAAGGA TCTCAAGAAG ATCCTTTGAT    4500
CTTTTCTACG GGGTCTGACG CTCAGTGGAA CGAAAACTCA CGTTAAGGGA TTTTGGTCAT    4560
GAGATTATCA AAAAGGATCT TCACCTAGAT CCTTTTAAAT TAAAAATGAA GTTTAAATC     4620
AATCTAAAGT ATATATGAGT AAACTTGGTC TGACAGTTAC CAATGCTTAA TCAGTGAGGC    4680
ACCTATCTCA GCGATCTGTC TATTTCGTTC ATCCATAGTT GCCTGACTCC CCGTCGTGTA    4740
GATAACTACG ATACGGGAGG GCTTACCATC TGGCCCCAGT GCTGCAATGA TACCGCGAGA    4800
CCCACGCTCA CCGGCTCCAG ATTTATCAGC AATAAACCAG CCAGCCGGAA GGGCCGAGCG    4860
CAGAAGTGGT CCTGCAACTT TATCCGCCTC CATCCAGTCT ATTAATTGTT GCCGGGAAGC    4920
TAGAGTAAGT AGTTCGCCAG TTAATAGTTT GCGCAACGTT GTTGCCATTG CTACAGGCAT    4980
CGTGGTGTCA CGCTCGTCGT TTGGTATGGC TTCATTCAGC TCCGGTTCCC AACGATCAAG    5040
GCGAGTTACA TGATCCCCCA TGTTGTGCAA AAAAGCGGTT AGCTCCTTCG GTCCTCCGAT    5100
CGTTGTCAGA AGTAAGTTGG CCGCAGTGTT ATCACTCATG GTTATGGCAG CACTGCATAA    5160
TTCTCTTACT GTCATGCCAT CCGTAAGATG CTTTTCTGTG ACTGGTGAGT ACTCAACCAA    5220
```

| GTCATTCTGA | GAATAGTGTA | TGCGGCGACC | GAGTTGCTCT | TGCCCGGCGT | CAATACGGGA | 5280 |
| TAATACCGCG | CCACATAGCA | GAACTTTAAA | AGTGCTCATC | ATTGGAAAAC | GTTCTTCGGG | 5340 |
| GCGAAAACTC | TCAAGGATCT | TACCGCTGTT | GAGATCCAGT | TCGATGTAAC | CCACTCGTCG | 5400 |
| ACCCAACTGA | TCTTCAGCAT | CTTTTACTTT | CACCAGCGTT | TCTGGGTGAG | CAAAAACAGG | 5460 |
| AAGGCAAAAT | GCCGCAAAAA | AGGGAATAAG | GGCGACACGG | AAATGTTGAA | TACTCATACT | 5520 |
| CTTCCTTTTT | CAATATTATT | GAAGCATTTA | TCAGGGTTAT | TGTCTCATGA | GCGGATACAT | 5580 |
| ATTTGAATGT | ATTTAGAAAA | ATAAACAAAT | AGGGGTTCCG | CGCACATTTC | CCCGAAAAGT | 5640 |
| GCCACCTGAC | GTC | | | | | 5653 |

(2) INFORMATION FOR SEQ ID NO:4:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (xi) SEQUENCE DESCRIPTION: SEQ ID NO:4:

| GGGGTCTCTC | TGGTTAGACC | AGATCTGAGC | CTGGGAGCTC | TCTGGCTAAC | TAGGGAACCC | 60 |
| ACG | | | | | | 63 |

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

ACTGCTTAAG CTCATGGCAG        20

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

AGGGAACCCA GTGCTTAAGC TTG        23

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:7:

CGTTCTGTGT TGGATCCCAT GGCAGG        26

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:8:

```
GTTTAGTAAG TCAAGCTTAA GTG                                                    2 3
```